United States Patent [19]
Podoleanu et al.

[11] Patent Number: 5,975,697
[45] Date of Patent: Nov. 2, 1999

[54] OPTICAL MAPPING APPARATUS WITH ADJUSTABLE DEPTH RESOLUTION

[75] Inventors: Adrian Gh. Podoleanu; David A. Jackson, both of Cantebury, United Kingdom

[73] Assignee: OTI Ophthalmic Technologies, Inc., Downsview, Canada

[21] Appl. No.: 09/199,153

[22] Filed: Nov. 25, 1998

[51] Int. Cl.$^6$ ..................................................... A61B 3/14
[52] U.S. Cl. .......................................................... 351/206
[58] Field of Search ..................................... 351/206, 207, 351/211, 212, 221, 246; 356/345, 346, 349, 357

[56] References Cited

U.S. PATENT DOCUMENTS

| | | |
|---|---|---|
| 5,268,738 | 12/1993 | Baney et al. . |
| 5,321,501 | 6/1994 | Swanson et al. . |
| 5,365,335 | 11/1994 | Sorin . |
| 5,459,570 | 10/1995 | Swanson et al. . |
| 5,469,261 | 11/1995 | Hellmuth et al. . |
| 5,491,524 | 2/1996 | Hellmuth et al. . |
| 5,493,109 | 2/1996 | Wei . |
| 5,537,162 | 7/1996 | Hellmuth et al. . |
| 5,644,642 | 7/1997 | Kirschbaum . |
| 5,760,901 | 6/1998 | Hill ........................................ 356/345 |

OTHER PUBLICATIONS

Paper entitled "Dispersion Effects . . . " by Ch. K. Hitzenberger published in proceedings SPIE 2981, pp. 29–36 (1997).
From book "Non–Invase Diagnostic . . . " in Chapter entitled Scanning Laser Ophthalmoscope by R.H. Webb pp. 438–450 ed B.R. Masters Springer–Verlag, New York (1990).
Paper entitled "Optical Coherence Tomography" by D. Huang in Science 254 p. 1178, (1991).
Paper entitled "Confocal Imaging of the Fundus . . . " by W.H. Woon in J., Brit. J. Ophthalmol., vol. 76 pp. 470–474 1992.
Paper entitled "Optical Coherence Domain . . . " by K. Hotate published in Journal of Lightwave Technology, vol. 11, No. 10, pp. 1701–1710, 1993.
Paper entitled "Three Electrode Laser . . . " by A. GH. Podoleanu in Conference Proceedings OFS–11, 11$^{th}$ International Conference on Opt. Fiber Sensors, pp. 312–315, May 21–24, 1996.
Paper entitled "Coherence Imaging by . . . " by A.GH. Podoleanu published in Opt. Letters, vol. 21, No. 21 pp. 1789–1791 1996.
Paper entitled "Optical Coherence Tomography" by AF Fercher in Journal of Biomedical Optics, 1(2), pp. 157–173 (1996).
Paper entitled "Simultaneous En–face . . . " by AGH Podoleanu in Opt. Letters, vol. 22, No. 13, pp. 1039–1041 (1997).
Paper entitled "Transversal & Longitudinal . . . " by A. GH. Podoleanu in Journal of Biomedical Optics, 3(1), pp. 12–20 (1998).
Paper entitled "Rapid & Scalable Scans . . . " by J. Ballif pub. in Opt. Letters., vol. 22 No. 11 pp. 757–759 (1997).
Paper entitled "In Vivo Endosopic . . . " by G. J. Tearney pub. in Science, vol. 276 pp. 2037–2039 (1997).
Paper entitled "Dispersion Induced Hiple . . . " by C.K. Hitzenberg pub. in Optics Communications pp. 179–185 Sep. 1998.
Paper entitled "En–Face Coherence Imaging . . . " by A. GH. Podoleanu in Opt. Letters, vol. 23, pp. 147–149 (1998).

*Primary Examiner*—George Manuel
*Attorney, Agent, or Firm*—Donald E. Hewson

[57] ABSTRACT

Optical mapping apparatus with adjustable depth resolution is provided. The optical mapping apparatus can display transversal images in an object, particularly the eye. The apparatus can deliver two or more images with different depth resolutions, or a combination of these images, or only one image with adjustable depth resolution. There is also provided optical mapping apparatus with adjustable depth resolution, where OCT images are corrected for the curvature at the back of the eye lens.

112 Claims, 13 Drawing Sheets

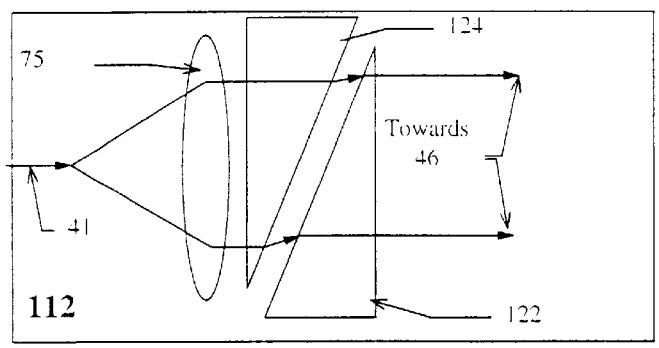
Figure 16. A priori art.
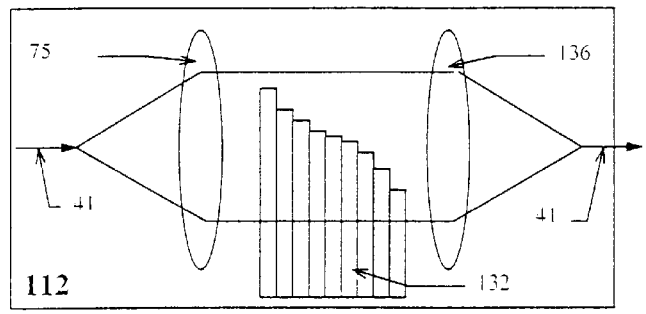
Figure 17.
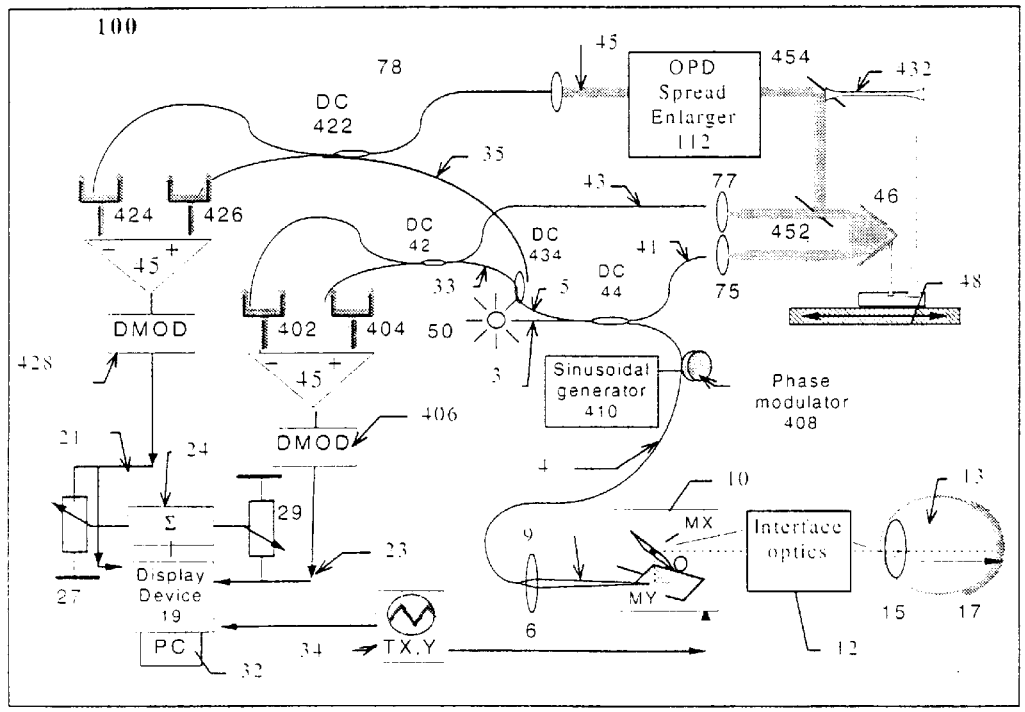
Figure 18.

OPTICAL MAPPING APPARATUS WITH ADJUSTABLE DEPTH RESOLUTION

FIELD OF THE INVENTION

This invention relates to an optical coherence tomographic apparatus and methods which can be used to supply images with adjustable depth resolution and/or superimposed images with different depth resolution from different objects, with applicability to biological investigations and particularly, but not exclusively, to eye retinal mapping.

This description refers mainly to the eye as the object. This has to be understood as merely a way to help the description and not as a restriction of the application of the present invention. Where "eye" is mentioned, a more general transparent and scattering object may be sought instead.

For eye fundus investigation, visual scientists and ophthalmologists are using scanning laser ophthalmoscopes (SLO), which are confocal imaging systems. A SLO system, as described in the chapter "Scanning laser ophthalmoscope" by R. H. Webb, pp. 438–450 in the vol. "Noninvasive diagnostic techniques in ophthalmology", ed. B. R. Masters, Springer-Verlag, New York, (1990) and in the paper "Confocal imaging of the fundus using a scanning laser ophthalmoscope" 6 by W. H. Woon, F. W. Fitzke, A. C. Bird and J. Marshall, in J., Brit. J. Ophthalmol. vol. 76, (1992), pp. 470–474, provides an indirect en-face image by scanning a laser beam across the eye, and the depth resolution of the existing commercial instruments is 300 $\mu$m, given the limited entrance aperture of the eye.

A recent advance in depth resolution has been provided by optical coherence tomography (OCT) as shown in the paper "Optical coherence tomography" by D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, Science 254, (1991), pp. 1178 and in the paper "Optical coherence tomography" by A. F. Fercher, in J. Biomed. Opt., 1(2), (1996), pp. 157–173. OCT has the potential of achieving much better depth resolution, as the limit in this case is not set by the eye any more, but by the coherence length of the source. (Superluminiscent diodes and mode-locked lasers are now available with coherence lengths less than 20 $\mu$m and 5 $\mu$m respectively).

There is a growing interest in the application of OCT by vision scientists and research ophthalmologists as the increased depth resolution of the OCT promises to provide information on structures of the eye not discernible with the state of the art SLO. It is believed that this depth resolution would advance our understanding of how retinal structure contributes to visual function in the human eye, both normal and abnormal. An OCT is now commercially available (Humphrey Instruments), which produces longitudinal images only, i.e.: images in the planes (x,z) or (y,z), where the z axis is perpendicular to the patient's face and x and y axes are in the plane of the patient's face. Examples of such apparatus for longitudinal and transversal imaging arc described in U.S. Pat. No. 5,493,109, U.S. Pat. No. 5,537,162, U.S. Pat. No. 5,491,524, U.S. Pat. No. 5,469,261, U.S. Pat. No. 5,321,501, and U.S. Pat. No. 5,459,570.

The paper entitled "Simultaneous En-face Imaging of Two Layers in Human Retina", by A. Gh. Podoleanu, G. M. Dobre, D. J. Webb, D. A. Jackson, in Opt. Letters, (1997), vol. 22, No. 13, pp. 1039–1041 and the paper entitled "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, Journal of Biomedical Optics, (1998), 3(1), pp. 12–20, report transversal OCT imaging of the living retina. These papers also demonstrate that, owing to the low coherence length, the OCT transversal images show only fragments of the retina and are difficult to interpret. In addition, due to the curvature of the retina at the back of the eye lens and due to the angular path variation of the scanned ray, the OCT transversal images show arcs at the extremities of the field investigated when the angular scanned field is larger than, say 6°. For example, for an eye lens of 2 cm focal length, the coherence plane curves in the form of an arc where at maximum angular deviation, of +/−3°, the distance from the plane is larger than 70 $\mu$m, which is much higher than the coherence length of the most super luminescent diodes on the market. These transversal images may be of use for the ophthalmologists only if the fragments sampled by the OCT from the fundus are uniquely placed in correspondence with fundus images produced by fundus cameras or with the SLO images. Such a correspondence is even more difficult to implement due to the inadvertent movement of the eye during investigation.

Unlike those provided by OCTs, the images provided by fundus cameras and SLOs are of much coarser depth resolution and they show the overall aspect of the retina. At the present time, the SLO and OCT depth resolutions are in a ratio of more than 10 and the depth resolution of OCT is not adjustable. This makes the appearance of OCT and SLO images very different and their comparison impractical. The OCT is a new tool in the investigative ophthalmology while the SLOs have been in use for at least a decade and have been used extensively in the eye diagnosis.

The utilization of OCT and SLO instruments in parallel, via some transfer optics elements, although possible, presents the following disadvantages:

the transfer optics elements may disturb the OCT and SLO images and these disturbances may be different for OCT and SLO;

the images cannot be superimposed in real time, as SLO works at video rate, 15 kHz, whilst the line scanning rates for the OCT are below a few hundred Hz.

The photodetected signal in the OCT can be used to produce an intensity image, but due to the high noise in the system, the reference beam needs to be blocked and consequently the SLO and OCT images cannot be generated at the same time.

There are known OCT systems with CCD cameras collecting parts of the returned signal from the object (eye/retina) in parallel and simultaneously with the OCT image. The images collected by the CCD and the OCT images in the known OCT systems are not pixel-by-pixel correspondent, as the optics used for the CCD camera are different from the optics used for the OCT. In addition, the wavelengths of the two systems are different, which results in differences between the two images. As another drawback, the fact that the CCD works at video rate and the OCT at a lower rate makes the interpretation and processing of the images difficult.

Another problem lies with the correction of images for movements when investigating moving targets, as for instance to correct for the microcascades when imaging the eye. For SLOs, software packages are used to align the images in a stack of sequences taken from the eye, based on corrections worked out involving correlation between successive images. However, the affectivity in correction is limited as the procedure involves correcting a system using information supplied by the same system.

Another problem with existing OCT systems is in the longitudinal scanning means. Fast scanning devices have been presented in literature, as disclosed in the paper "Rapid and scalable scans at 21 m/s in optical low-coherence reflectometry", by J. Ballif, R. Gianotti, Ph. Chavanne, R. Walti and R. P. Salathe, published in Op. Lett., Vol. 22, (1997), No. 11, pp. 757–759, where multiple paths in a rotating cube are employed, however this approach is compromised by a variation in dispersion while the path is changed. A relatively fast scanning device is the object of the U.S. Pat. No. 5,491,524 where a special helical mirror is disclosed. This mirror is quite cumbersome and difficult to manufacture and the cost is high. A fast longitudinal scan at kHz rate is reported in the paper "In vivo endoscopic optical biopsy with optical coherence tomography", by G. J. Tearney, M. E. Brezinski, B. E. Bouma, S. A. Boppart, C. Pitris, J. F. Southern and J. G. Fujimoto, published in Science, vol. 276, (1997), pp. 2037–2039, where a galvanometer scanner in association with a lens and a grating is used. However, the device is expensive and the grating introduces attenuation. In addition, all these fast devices refer to light taken from one arm (fiber) and relaunched in the same arm (fiber), making the devices, in their present form, incompatible with the high performance OCT systems using balance detection where the reference beam comes from a first arm (fiber) of the OCT and is sent to a second arm (fiber).

Thus, a need exists to provide low cost, fast and non-attenuating longitudinal scanning.

Thus, a need exists for procedures to help the interpretation of OCT transversal images and to ease their comparison with the SLO images for which large data bases for diagnostics have been created.

The present invention sets out to solve the above problems and relates to methods and apparatus to produce, process and eventually superimpose an image of high depth resolution, such as that produced by the OCT onto an image of poorer depth resolution, such as that created by a confocal optical receiver, or to produce, process and eventually superimpose OCT images of different depth resolution and to produce sequentially either an image of high depth resolution, such as that produced by the OCT or an image of poorer depth resolution, such as that created by a confocal optical receiver.

The present invention provides an optical mapping apparatus with adjustable depth resolution, comprising: an interferometer chosen from the group consisting of fiberized interferometers and bulk interferometers, wherein said interferometer is excited by an optical source with adjustable coherence length, said interferometer comprising a first optical path and a second optical path leading to an object location, and to a reference reflector, respectively; raster scanning means for transversally scanning an optical output from the said interferometer over a predetermined area about a point in a raster, or for moving the optical output from the interferometer to a point in a raster; interface optics for transferring an optical beam from the raster scanning means to an object situated at the object location and for transferring an optical output beam reflected and scattered from the object back to the interferometer, along said first optical path; means to alter at least one of the first optical path and the second path, so as to introduce intensity modulation, or phase modulation, or intensity modulation and phase modulation; analyzing means, coupled to said raster scanning means, for demodulating the photodetected signal; means for longitudinal scanning, to alter the length of the first optical path or the second optical path over a predetermined amount, for at least one of the points in the raster, in steps or continuously, at a pace synchronised with transversal scanning means; and means for displaying or storing an image of at least part of said object.

In another alternative of the present invention there is provided an optical mapping apparatus with adjustable depth resolution, comprising: an interferometer chosen from the group consisting of fiberized interferometers and bulk interferometers, wherein said interferometer is excited by an optical radiation source or a source with adjustable coherence length, said interferometer comprising a first optical path and a second optical path leading to an object location and to a reference reflector, respectively; a confocal optical receiver with adjustable focal depth; an optical splitter for internally directing light returned from an object situated at said object location to said optical confocal receiver; raster scanning means for raster scanning an optical output from the interferometer over a line, or over a predetermined area; interface optics for transferring an optical beam from said raster scanning means to the object and for transferring an optical output beam reflected and scattered from the object back to said optical splitter through said raster scanning means, and from said optical splitter to both of said interferometer and said optical confocal receiver, in a ratio determined by said optical splitter; means to alter at least one of the first optical path and the second optical path, to introduce intensity modulation, or phase modulation, or intensity modulation and phase modulation; analyzing means, coupled to said raster scanning means, for demodulating the photodetected signal; means for longitudinal scanning, to alter the length of the first optical path or the second optical path over a predetermined amount, for at least one point in the raster, in steps or continuously, at a pace synchronised with transversal scanning means; means for processing an image created by said interferometer and an image created by said confocal receiver; and means for the simultaneous display of the said respective images created by said interferometer and by said confocal receiver.

Yet another embodiment of the invention provides an optical mapping apparatus with adjustable depth resolution comprising: an interferometer chosen from the group consisting of fiberized interferometers and bulk interferometers, wherein said interferometer is excited by an optical source chosen from the group consisting of broadband optical sources and sources having adjustable coherence length; wherein said interferometer comprises a first optical path and a second optical path leading to an object location, and to a reference reflector, respectively; an optical element for producing an enlargement of the correlation function of the optical source when placed in either of said first path or said second path; raster scanning means for transversally scanning an optical output from said interferometer over a predetermined area; interface optics, for transferring an optical beam from said raster scanning means to an object situated at said object location, and for transferring an optical output beam reflected and scattered from said object back to said interferometer, along said first optical path; means to alter at least one of said first optical path and said second optical path, to introduce intensity modulation, or phase modulation, or intensity modulation and phase modulation; analyzing means, coupled to said raster scanning means, for demodulating the photodetected signal; means for longitudinal scanning, to alter the length of the first optical path or the second optical path over a predetermined amount, for at least one point in the raster, in steps or continuously, at a pace synchronised with transversal scanning means; and means for displaying or storing an image of at least part of said object.

Still another embodiment of the present invention provides an optical mapping apparatus with adjustable depth resolution comprising: at least two interferometers excited by an optical source consisting of broadband optical sources and sources having adjustable coherence length; wherein each of said interferometers comprises an at least partly common first optical path leading to an object location, and a respective second optical path for each interferometer, wherein each of said second optical paths leads to a respective reference reflector; at least one device for producing an enlargement of the correlation function of the source when placed in at least one of said optical second paths; adjustable raster scanning means for transversally scanning an optical output from said interferometers over a predetermined area; interface optics for transferring an optical beam from said raster scanning means to an object situated at the object location, and for transferring an optical output beam reflected and scattered from the object back to said interferometers, along said first optical path; means to alter said first optical path, or one of said second optical paths, to introduce intensity modulation, phase modulation, or intensity modulation and phase modulation; analyzing means, coupled to said raster scanning means, for demodulating the photodetected signal; longitudinal scanning means to alter the length of said first optical path or said second optical path in each interferometer simultaneously over a predetermined amount, for at least one point in the raster, in steps or continuously, at a pace synchronised with transversal scanning means; and means for displaying or storing image of at least part of said object.

In keeping with certain provisions of the present invention, the optical source comprises two superposed radiation sources, one of which has a very short coherence length, and the other of which has a coherence length greater than that of the first source. Both sources have essentially the same central wavelength.

Moreover, the coherence length of at least one of the optical sources is electrically adjustable to provide either a continuous range for the compound source from less than a few micrometers or a few tens of micrometers, to more than a few hundreds of micrometers, or to provide adjustability on some sub-intervals, by applying a combination of currents thereto.

When the optical source comprises an electronic unit, and there are two superposed radiation sources, the electronic unit will change the ratio of the powers of those two radiation sources. If so, when the ratio is changed, the electronic unit ensures that the overall intensity is kept constant, or that the bias intensity in the final image is kept constant.

An optical source, in keeping with the present invention, may comprise an electro-optic element for balancing the contribution of the two component sources in the final output beam. The electro-optic element may be an electronically controllable directional coupler.

As is discussed hereafter, the optical source may comprise two first fibers, where each first fiber is arranged for transmitting light from a respective optical source, together with a second fiber for collecting light from the source fibers. A second fiber is translatable between the first fibers.

Moreover, the optical source may comprise two first fibers, each of which is arranged for transmitting light from a respective source, together with a collecting mirror for collecting light from the first fibers.

Where there are two superposed radiation sources, the output beams thereof may be oriented and focused to ensure an intersection of areas of their spacial distribution power.

Still further, the optical source with adjustable coherence length, as used in the present invention, may be a multi-electrode laser diode.

Moreover, the optical source having an adjustable coherence length may be a subnanosecond tunable optical source which is adapted to be tuned under subnanosecond electric pulse control in a bandwidth for which the associated correlation profile width secures a predetermined depth resolution.

Under one aspect of the present invention, the first optical source of largest bandwidth may be modulated in intensity at a first frequency, and the second source of narrowest bandwidth may be modulated in intensity at a second frequency. The first and second frequencies are different, and their ratio is an irrational number. Moreover, the photodetected signal is sent to a first receiver which is tuned on the first frequency and a to a second receiver which is tuned on the second frequency, so as to select corresponding images. The first corresponding image has a very narrow sectioning interval given by the first receiver tuned on the first frequency, and the second corresponding image has a wider sectioning interval given by the second receiver tuned on the second frequency. Still further, the first and second corresponding images are displayed simultaneously by way of a two-input display device.

In any optical mapping apparatus according to the present invention, the optical source may be broadband; and in any optical mapping apparatus according to the present invention, the optical splitter may be a bulk beam splitter.

Further, the optical splitter may be a fiberized directional coupler terminated on a pigtailed photodetector provided on the optical confocal receiver, when used. The fiber input of that directional coupler acts as the aperture of the confocal optical receiver, and the optical splitter is part of the first optical path of the interferometer. The image given by the confocal optical receiver may be used in the storage process of the image given by an OCT channel, to compensate during its acquisition for the transversal object movement.

In any optical mapping apparatus of the present invention, the means for processing an image can perform mathematical operations in a pixel-by-pixel format, using the interferometer image and the confocal optical receiver image.

Moreover, the means for processing images can also perform mathematical operations in a pixel-by-pixel format, using the image obtained by the storage process.

In an optical mapping apparatus according to the present invention, the confocal receiver may comprise an adjustable pin-hole behind a lens or behind a lens and a photodetector, and the focal depth interval is adjustable independently of the interferometer.

The confocal receiver may comprise a fiber pigtail terminated on a photodetector.

In any optical mapping apparatus according to the present invention, there is a reference beam for the interferometer, and the apparatus may further be provided with means to block the reference beam. If so, when the blocking means is activated, it will synchronously switch the input of the display device to the output of a high gain amplifier for the photodetected signal.

In keeping with the present invention, an interferometer may use balance detection, and the amplifier associated therewith will provide the addition of the photodetected signals so that the result will then be sent to a displaying device.

As noted hereafter, when photodetectors are employed in avalanche, their gain is switched automatically by a reference power via the voltage drop of the series resistors connected therewith. This will occur when the optical mapping apparatus is switched between a confocal regime of operation and an OCT regime of operation.

When the interferometer being used is a bulk interferometer, the depth resolution of the image obtained with the reference arm thereof blocked can be adjusted by varying the numerical aperture of optics which precede the photodetector, when the photodetector is used, or by simultaneously varying the numerical aperture of optics preceding to photodetectors when balance detection is employed. The numerical apertures are varied by adjusting either the focal length of the lens or by adjusting the diameter of the pin hole in the optics preceding the photodetector or photodetectors when balance detection is used.

When the optical source is broadband, the depth resolution in a final image produced by the optical mapping apparatus of the present invention may be adjustable by one of several steps, including: (i) adjusting the depth sectioning interval of the image produced by the confocal optical receiver; or (ii) balancing the amplitudes of an interferometer image signal and of an optical confocal receiver signal sent to display means, so as to provide an adjustable resolution depth from a minimum given by the coherence length of the broadband source to a maximum given by the confocal optical receiver.

Also, as noted hereafter, the depth resolution of a final image produced by optical mapping apparatus of the present invention may be adjustable by balancing the amplitudes of an interferometer image signal and of an optical confocal receiver signal sent to a display means. This provides an adjustable resolution depth from a minimum given by the coherence length of the broadband source to a maximum given by the confocal optical receiver.

The depth resolution of a final image produced by an apparatus in keeping with the present invention may also be adjustable by one of the following steps: (i) varying the sectioning interval of an interferometer image by changing the coherence length of its source; or (ii) weighting the contributions of the interferometer and confocal optical receiver to a compound image, so as to provide an adjustable resolution depth from a minimum given by the minimum coherence length of the first source to a maximum given by either the confocal optical receiver or the maximum length of the second source.

When an optical splitter is employed, it may have an optimised splitting ratio, so as to thereby ensure optimal signal-to-noise ratios in images which are generated by both the interferometer and the optical confocal receiver.

In one embodiment of the present invention, an optical element for enlarging the correlational profile of the optical source may be employed. If so, that optical element may be a dispersive element which causes an increase in the associated coherence length. Otherwise, the optical element for enlarging the correlation profile of the optical source may be a multi-step echelon.

Where a dispersive element is used, it can be gradually introduced into the first or second optical paths of the interferometer, for a continuous adjustment of the coherence length and, consequently, of the depth resolution in an image generated by the optical mapping apparatus.

In an optical mapping apparatus of the present invention, where the first optical path is completely shared by the interferometers, then analyzing means is employed which uses a single photoreciever for all of the interferometers, and for each of the second optical paths. Such apparatus comprises a phase modulator in each interferometer, where each respective phase modulator is driven at a different frequency which is sufficiently distant apart from the other phase modulator frequencies so that the analyzing means is able to separate the respective signals in the interferometers, by means of subsequent frequency bandpass filtering.

Accordingly, such apparatus will comprise means for processing signals in the interferometers using mathematical operations in a pixel-by-pixel format, and in a controllable ratio using respective images created by each interferometer.

In optical mapping apparatus according to the present invention, an image in one of the interferometers which has the poorest depth resolution, and which is obtained by the optical element for enlarging the correlation profile, may be used in a process for storing an image with the best depth resolution which was obtained using another interferometer with no such optical element. This will compensate for transversal object movement during image acquisition.

Thus embodiments of the invention provide:

a unique OCT system with adjustable depth resolution from the minimum achievable with the largest bandwidth optical source used in the system up to values exceeding the depth resolution of the confocal scanning systems providing sequential or simultaneous images with different depth resolution;

an apparatus including both an OCT and an optical confocal system which both share the same collecting optics;

an apparatus including two or more OCTs, each creating independent OCT images with different depth resolution covering a range from the minimum achievable with the largest bandwidth optical source used in the system up to values exceeding the depth resolution of the confocal scanning systems.

For preferred embodiments, the measurements involve non-invasive cross-sectional imaging in biological specimens with one particular application in the eye imaging and more specific for the retina imaging.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 16 shows an element to enlarge the correlation function of a broadband source;

FIG. 17 shows another element to enlarge the correlation function of a broadband source;

FIG. 18 shows a further embodiment of the present invention;

DETAILED DESCRIPTION OF THE PREFERRED EMBODIMENTS

Components which are the same in the various figures have been designated by the same numerals for ease of understanding.

Where optical fibers are used, this is only as an example and it should be noted that a bulk implementation is equally feasible, in which case the respective elements in the examples using fiberized components, are to be replaced by optical paths and the couplers by plate beamsplitters.

An OCT involves and makes use of techniques known in the art and as described in U.S. Pat. No. 5,459,570, U.S. Pat. No. 5,321,501, U.S. Pat. No. 5,491,524, U.S. Pat. No. 5,493,109, U.S. Pat. No. 5,365,335, U.S. Pat. No. 5,268,738, and U.S. Pat. No. 5,644,642, can be constructed in bulk or optical fiber, has means for transversally scanning the target, has means for longitudinal scanning of the reference path length, has means for phase modulation, has means for controlling the polarization stage as bulk or fiber polarizer controllers and has means for compensating for dispersion.

Figure 1A:
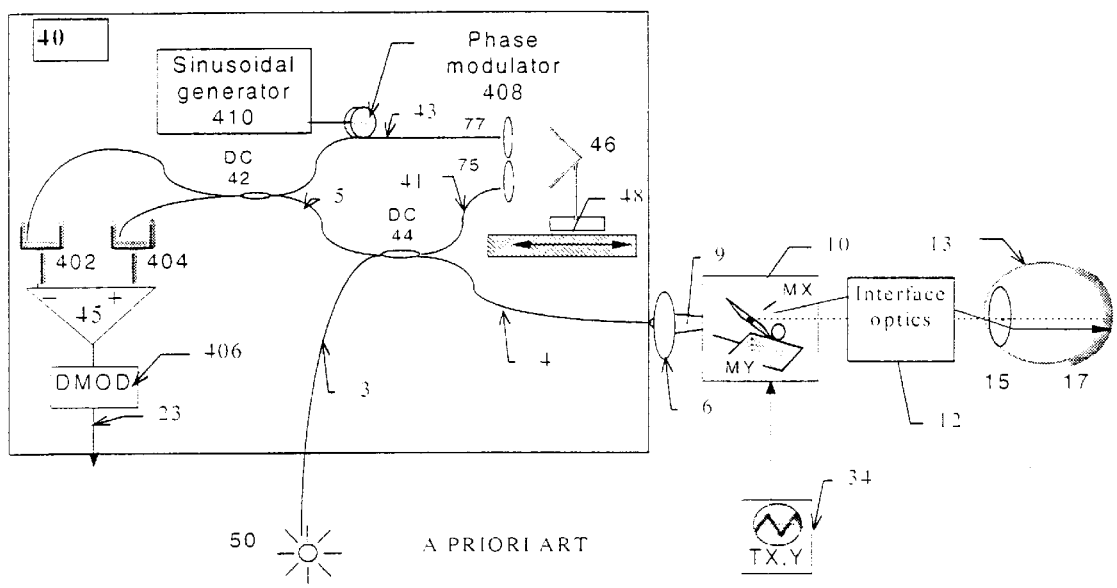
FIG. 1A is a diagram of embodiment of an OCT using both optic fiber and bulk components.
Figure 1B:
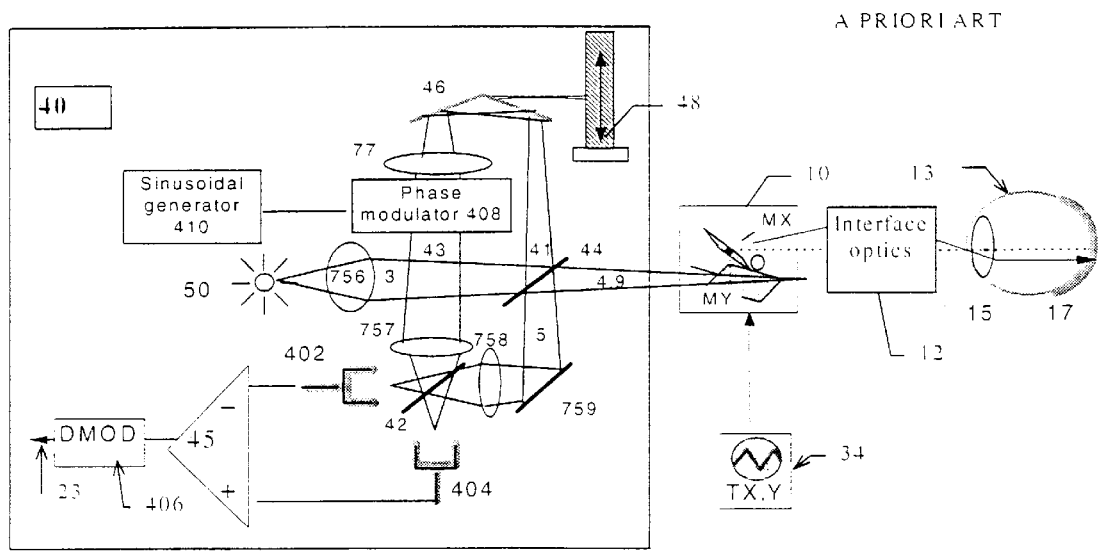
FIG. 1B is a diagram of embodiment of an OCT using only bulk components.

A fiber and a bulk implementation of an OCT 40 are shown in FIGS 1A and 1B, respectively, where the source 50 is broadband and coupled to an optical coupler (beamsplitter) 44. The source has a central wavelength suitable for the particular object to be investigated. For eye investigation, a wavelength in the near infrared, such as 800–900 nm, is selected. The broadband source 50 may be for example one or more light emitting diodes, super luminescent diodes, bulb lamps or short-pulse lasers combined to produce the largest possible bandwidth and minimum spectrum ripple by techniques known in the art.

The light received by the coupler (beamsplitter) 44 is split into a first fiber optic path (or free space path) 4 leading to scanning sample assembly 10 which includes means known in the art, as galvanometer scanners, polygon mirrors, resonant scanners, acousto-optic modulators, rotating or vibrating prisms, etc. The scanner head is under the control of triangle, sawtooth or DC voltages produced by a generator 34. The second optic output of coupler (beamsplitter) 44, a fiber (path) 41, leads to a focusing element 75 and to a reference reflecting assembly 46, mounted on a translation stage 48. Other means of altering the reference optical path can be used, in the form of well known optical devices and components, such as, vibrator, helical (U.S. Pat. No. 5,491, 524) or other shapes of conveniently designed mirrors, fiber wrapped around piezo-cylinders or a galvanometer mirror-grating arrangement developed for femtosecond pulse shaping as disclosed in the paper "In vivo endoscopic optical biopsy with optical coherence tomography", by G. J. Tearney, M. E. Brezinski, B. E. Bouma, S. A. Boppart, C. Pitris, J. F. Southern and J. G. Fujimoto, published in Science, vol. 276, (1997), pp. 2037–2039, or by using the arrangements shown in FIGS. 21, 22 or 23, based on galvanometer mirror, lens and mirrors in a suitable arrangement to receive the light from one fiber and send it back to the OCT via a different fiber. The light reflected by the reference assembly 46 is injected into a second coupler (beamsplitter) 42 via an optical focusing element 77, fiber (path) 43, where the coupler (beamsplitter) 42 is tied to the coupler (beamsplitter) 44 via a fiber (path) 5. The outputs of the coupler (beamsplitter) 42 are applied to photodetectors 402 and 404 whose outputs are tied to the inputs of a differential amplifier 45. For a coupler (beamsplitter) 42 with 50% coupling ratio, an ideal balanced detection technique is implemented The fiber (path) 4 and fiber (path) 5, along with the scanning head 10 and interface optics 12 define an object path, returning the object signal. The scanning head 10 can be divided in two parts separated by optical elements like lenses and/or mirrors in configurations known in the SLO art or general raster scanning systems, in which case the scanner head 10 and interface optics 12 are interleaved to each other, in one block, and only for convenience they are represented here separately. The fiber (path) 41, assembly 46 and fiber (path) 43 constitute a reference path and are circulated by the reference signal. The object signal interferes with the reference signal in the optical coupler (beamsplitter) 42, when the optical path difference (OPD) between the reference path and object path is less than the coherence length of the source 50.

To maximize interference, the polarization in the interferometer is adjusted using polarization controller devices (not shown).

For the bulk version shown in FIG. 1B, focusing elements are needed for the source 756, and for the photodetectors 757 and 758.

In the OCT shown in FIG. 1A, the optical fiber of path 43 is wrapped around a piezoelectric crystal transducer or actuator 408 which vibrates in response to the electric signal applied by a sinusoidal generator 410, to produce the phase modulation necessary to facilitate interference detection. However, the phase modulator can be placed anywhere in the reference path or in the object path. Other means of phase modulation can also be used, as fiberized phase modulators, fiber stretchers or bulk crystals, these being used with preference in the bulk version as shown in FIG. 1B, as electro-optical, acousto-optical, or magneto-optical modulators, or vibration of the reflecting mirrors in the reference assembly 46.

Alternatively, the modulation introduced by the transversal scanner head 10 can be used as shown in the papers "Coherence Imaging by Use of a Newton Rings Sampling Function" by A. Gh. Podoleanu, G. M. Dobre, D. J. Webb, D. A. Jackson, published in Opt. Lett., Vol. 21, No. 21, (1996), pp. 1789–1791 and "En-face Coherence Imaging Using Galvanometer Scanner Modulation" by A. Gh. Podoleanu, G. M. Dobre, D. A. Jackson, Opt. Lett., 23, pp. 147–149, 1998.

As opposed to the majority of implementations mentioned in previous publications and patents on OCT where the reference path is scanned (longitudinal scanning) at a sufficiently high speed to introduce a Doppler shift subsequently used as a mean to generate the carrier and the transversal scanning is at a much lower speed than the longitudinal scanning, in the present invention, the Doppler shift introduced by the reference path is not employed and the transversal scanning of the object is much faster that the longitudinal scan. When generating a transversal OCT image, the optical path imbalance is advanced after the transversal raster is completed or the path imbalance is varied at such a low speed, that the path imbalance between the point in the object at the beginning of the raster and the point in the object at the end of the raster is less than or only a few times larger than the coherence length of the source.

In addition, as shown in the paper entitled "Transversal and Longitudinal Images from the Retina of the Living Eye Using Low Coherence Reflectometry", by A. Gh. Podoleanu, Mauritius Seeger, George M. Dobre, David J. Webb, David A. Jackson and F. Fitzke, published in the Journal of Biomedical Optics, (1998), 3 (1), pp. 12–20, 1998, if the image size is sufficiently large, there is no need for a supplementary device to introduce phase modulation and the phase modulation created by transversally scanning the object could be the only modulation employed.

As explained in the papers mentioned above, the OCT image results as the projection of a sampling function on the target. Due to the target profile, the sampling function varies across the target and consequently the frequency of the signal generated varies. The DC and low frequencies can be eliminated, as they correspond to low transversal definition and by doing so, the 1/f noise is also rejected.

In order to prevent dispersion, which can enlarge the correlation profile, lengths of glass in the object and reference paths should be substantially equal and eventual remaining dispersion in the glass and dispersion in the object should be compensated by means such as known in the art, using lengths of optical material with suitable index of refraction and dispersive properties placed anywhere in the reference path, as for instance between the elements 75, 77 and the assembly 46, or in the object path in the interface optics 12.

The OCT demodulation block 406 uses a band pass filter on the phase modulator carrier, then a rectifier and low pass filter, or band pass filters tuned on an even and odd multiple of the carrier frequency, followed by individual rectifiers and low pass filters and a summator (not shown), and by a processor, which can produce the linear, the squared, or logarithmic version of the signal amplitude.

Figure 2:
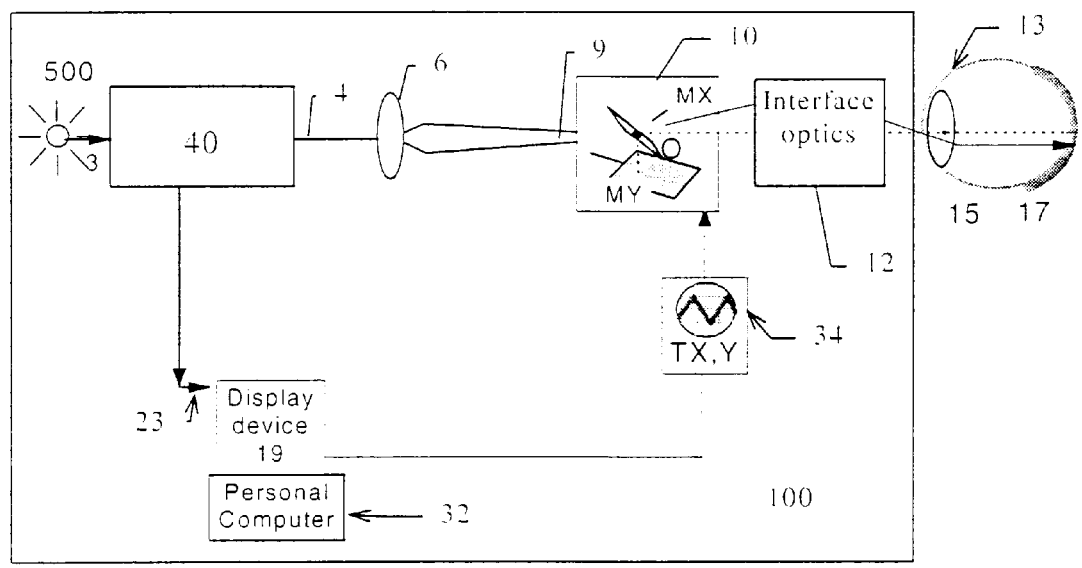
FIG. 2 shows an embodiment of an OCT tomographic mapping apparatus with adjustable depth resolution which is based on the OCT of FIG. 1 and which uses a source with adjustable coherence length.

FIG. 2 shows, in diagrammatic form, a first embodiment of an ophthalmic apparatus 100 in accordance with the present invention. As shown in FIG. 2, the apparatus 100 comprises an OCT interferometer 40 excited by a source 500 with adjustable coherence length. The image is displayed and recorded by means of a suitable display device 19, such as a frame grabber, a storage oscilloscope or a suitable printer. The display device 19 is under computer 32 control. Using a coherence length larger than, say 300 $\mu$m (the actual depth resolution of commercial SLOs), OCT transversal images with a depth resolution similar to those offered by existing SLO are obtained. Then, by reducing the coherence length, the depth resolution may be improved to determine the thickness of some features in the object volume (the retina). Various implementations of a source with adjustable coherence length as the source 500 in accordance with various embodiments of the invention are shown in FIGS. 3 through 8.

Figure 3:
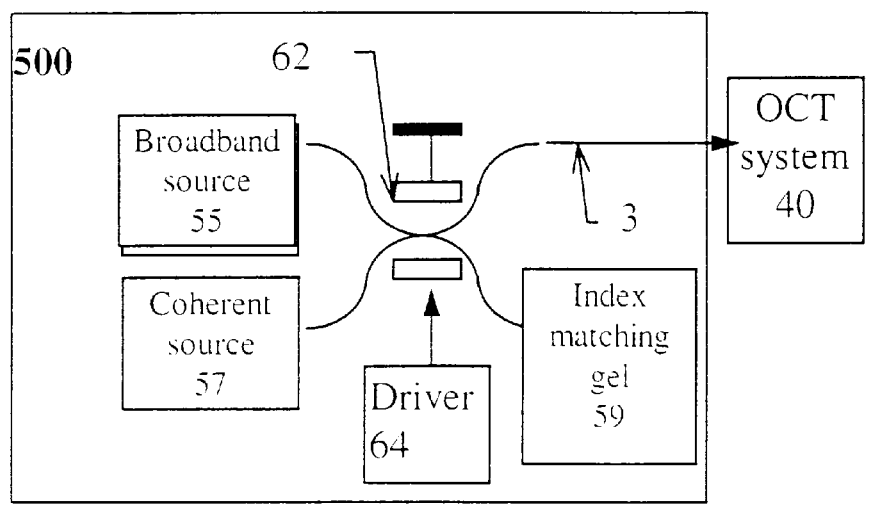
FIGS. 3, 4, 5, 6, 7 and 8 show alternative sources with adjustable coherence length for use in the present invention.

One embodiment of a source with adjustable coherence length, which is shown in FIG. 3 uses a combination of two sources, one broadband 55 (one or more lamps, SLDs or mode-locked lasers) and the other 57 with a larger coherence length (single mode laser diode or another type of laser with a coherent length larger than the coherence length of the broadband source 55; or a large bandwidth source as, for instance, an SLD, equipped with an optical filter or with a set of optical filters to narrow its linewidth). The optical powers are added via the electrically controlled directional coupler 62 with a suitable coupling ratio depending on the powers of the two sources, and delivered to the OCT 40, via the fiber 3. The coupler 62 is used to switch and weight the contribution of each field sent to the OCT 40, under the control of a driving unit 64.

In order to cover the entire scene of an image over 40° which is usually the angle field used in SLO, at least 300 $\mu$m coherence length will be necessary, taking into account a medium curvature of the wavefront at the back of an eye lens of focal length 2 cm and the heights of optical nerve layers. The two sources in FIG. 3 have the same central wavelength and the coherence length of the coherent source 57 must be restricted to prevent matching of a fiber end reflection, (when the interferometer in the OCT 40 is in fiber, or any other reflection from the faces of optical bulk elements when the interferometer is in bulk) with features inside the investigation volume. The coherence length of the source 500 is adjustable under the control of the electric field applied to the coupler 62. Weighting the powers delivered by the two optic sources 55 and 57, the equivalent coherence length of the overall optic field injected into the system is adjustable. In fact, two images are created, one with a narrow sectioning depth due to the source 55 and the other with a larger sectioning depth due to the source 57. Reducing the power of the first and increasing the power of the second, has the effect of bringing into view features from background of the image created with the broadband source.

Two or more optical sources are also used in the U.S. Pat. No. 5,459,570, however they are destined to display the wavelength dependence of the OCT image. To this end, the sources have different wavelengths and similar coherence lengths, as opposed to the present disclosure where the sources have substantially the same wavelengths but different coherence lengths. As other differences, in the U.S. Pat. No. 5,459,570 the demodulation method employed is based on the Doppler frequency generated when moving the reference mirror, and these Doppler frequencies are different for different wavelengths. Generally the sources were used sequentially. When used simultaneously, optical filters were used to select different wavelengths and bandpass filters tuned on the corresponding different Doppler frequencies were used to process the signal.

In the present disclosure, a cumulating OCT image produced by both sources is displayed without recurring to longitudinal mirror shift as in the U.S. Pat. No. 5459570, an unique bandpass filter for the signals produced by both sources is used to pass the bandwidth due to the phase modulation introduced by transversally scanning the object or tuned on the phase modulation frequency introduced by an external phase modulator.

Figure 4:
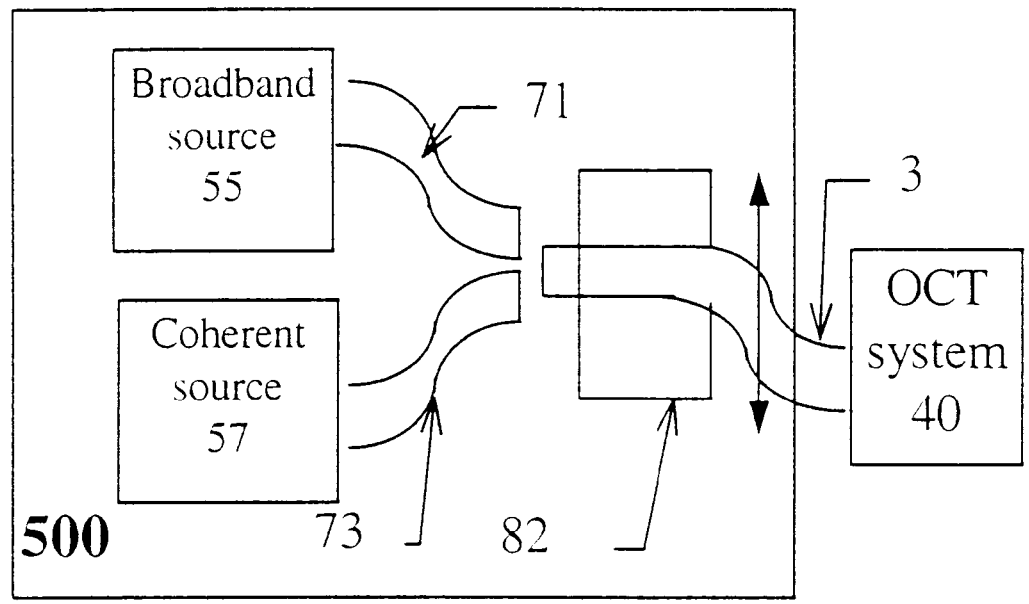

FIG. 4 shows a second embodiment of a source with adjustable coherence length 500, where a micrometer translation stage 82 is employed to shift and position the collecting fiber 3 input to the OCT system 40, in such a way to collect signals of different strengths from the output of the sources 55 and 57 via the fibers 71 respectively 72.

Figure 5:
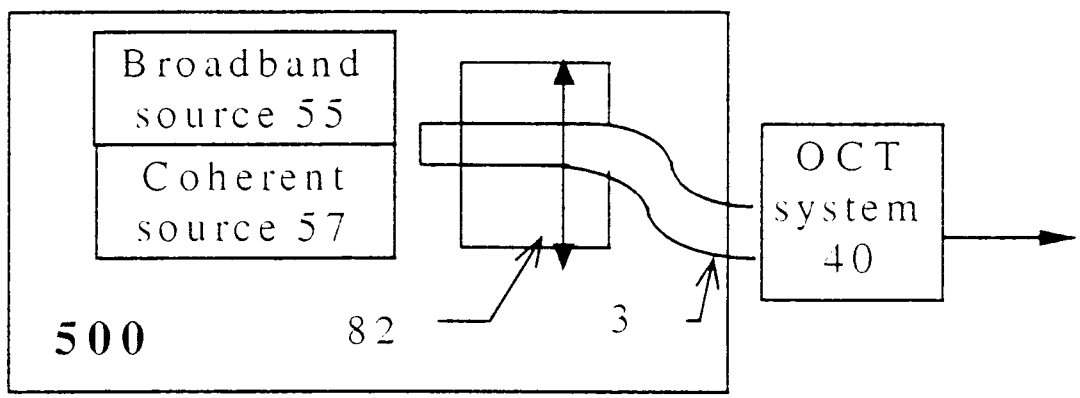

FIG. 5 illustrates an alternative embodiment of a source 500, where a micrometer translation stage 82 is employed to shift and position the collecting fiber 3, input to the OCT system 40, in such a way to collect signals of different strengths from the output of the sources 55 and 57, suitably orientated and equipped with micro optics elements to ensure a sufficient coupling of either source into fiber 3. Equivalently, when the two sources 55 and 57 are arranged in a line parallel to the direction of movement of the stage 82, the fiber 3 can be replaced with a mirror oriented at 45° to the direction of movement of the translation stage 82, which when moved in the direction shown by the double arrow, intercepts all or parts of the output beams of the two sources.

Figure 6:
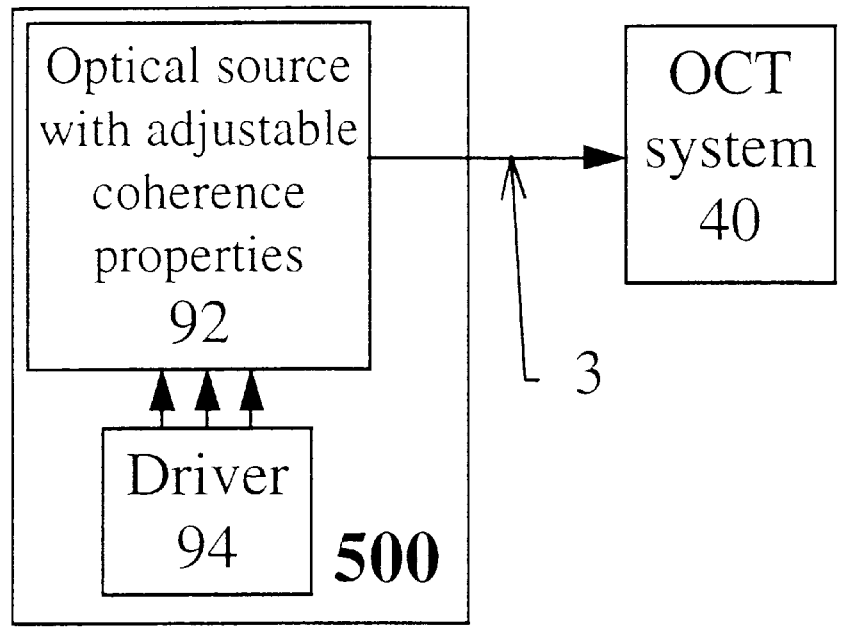

FIG. 6 details yet another embodiment of the source 500, where a special optical source, 92, with electrically adjustable coherence is used (for instance, a multi-electrode laser diode, which, depending on the driving conditions of different electrodes can supply a very coherent field or can deliver an incoherent field to the OCT 40). Such multi-electrode laser diodes can behave as an SLD (broadband source) or as a very coherent laser source. Three electrode diode lasers with adjustable spectrum are known and such a device with coherence length adjustable from 30 to 300 $\mu$m is described in the paper "Three Electrode Laser as a Source and Detection Unit for Low Coherence Interferometry" by A. Gh. Podoleanu, G. M. Dobre, D. A. Jackson, A. T. Semenov, S. A. Safin, V. R. Shidlovski, published in the conf. proceedings OFS-11,11th Intern. Conf. on Opt. Fibre Sensors, Sapporo, May 21–24, (1996), p. 312–315. The driver 94 ensures a suitable set of currents pass through the control pins of the source 92 to vary the coherence length. The source spectrum may have small satellite coherent peaks. If such extra peaks exist, they must appear at distances greater than the operational range of the system. For the retinal applications, 2 mm is a minimum and usually the solid state lasers have 1 mm width cavities which give repetition of correlation peaks at 2 mm. Laser sources with cavity lengths of greater than 2 mm can also be used.

Figure 7:
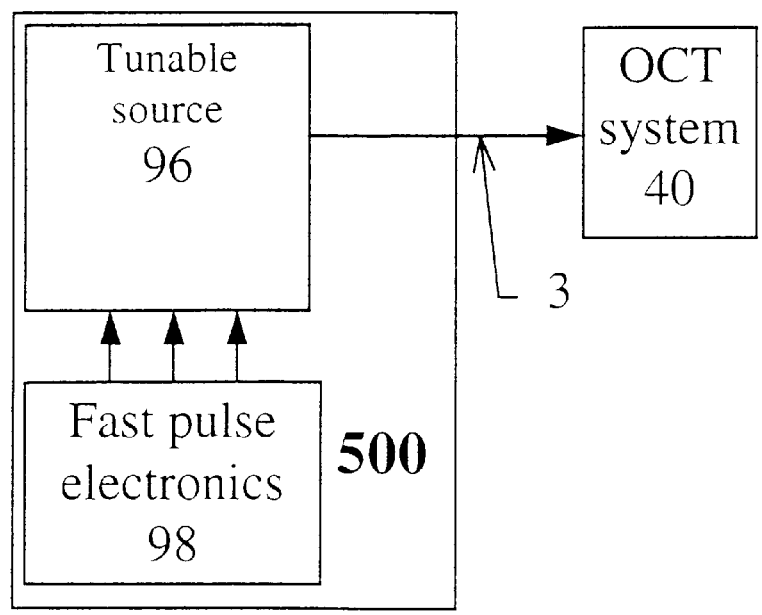

Another embodiment of a source with adjustable coherence length 500 is shown in FIG. 7, where a tunable source 96, is tuned at a rate faster than the bandwidth of the processing receiver in the OCT. One version for the tunable source 96 uses a multi-electrode laser diode or a DFB laser. The principle involved in this case is that of a source with synthesized coherence as described in the paper "Optical Coherence Domain Reflectometry by Synthesis of Coherence Function" by K. Hotate and O. Kamatani, published in J. Lightwave Technology, Vol. 11, No. 10, (1993), pp. 1701–1710. The driving electronics 98 are capable of applying very fast pulses to enlarge the source spectrum at the level necessary for a good OCT sectioning capability. Equivalent coherence lengths of 300 $\mu$m to a few meters are obtained in this way. The depth resolution of the apparatus is adjustable by changing the amplitude of modulation pulses applied.

Figure 8:
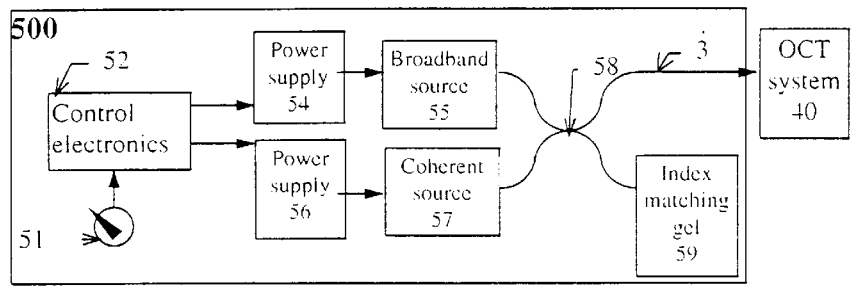

FIG. 8 shows another embodiment of a source with adjustable coherence length 500, where the two sources 55 and 57 are added via the directional coupler 58 with a suitable coupling ratio depending on the powers of the two sources, and delivered to the OCT 40, via the fiber 3. Alternatively, a beamsplitter can be used instead of the coupler 58 in which case 3 represents the optical output and the index matching gel 59 is not necessary. The coherence length of the source 500 is adjustable under the control of knob 51. The power dependence of the optical sources on the control parameter, adjusted via the drivers 54 and 56 of the respective optical sources, may be linear or nonlinear; for instance the SLD power dependence is more or less linear with the injecting current, while the laser diode dependence is very nonlinear. The same is true for the FWHM spectrum of a laser diode as an example of coherent source which can be used as source 57. The control electronics 52 ensures that a smooth dependence, preferably linear (or as deemed suitable for the applications or clinical use), is implemented across the range of rotation angle of the knob 51 and the range of depth sectioning interval adjusted in this way. The control electronics ensures also that for each position of the knob 51, the power at the output 3 is constant and it does not exceed the safety value on the retina for ophthalmic applications. For such applications, the coherence length should be adjustable from the minimum ensured by the broadband source 55 up to more than a few hundred of micrometers. Alternatively, one or both of the sources 55 and 57 in FIGS. 3, 4, 5, and 8 could be of the type presented in FIG. 6 and 7.

Figure 9:
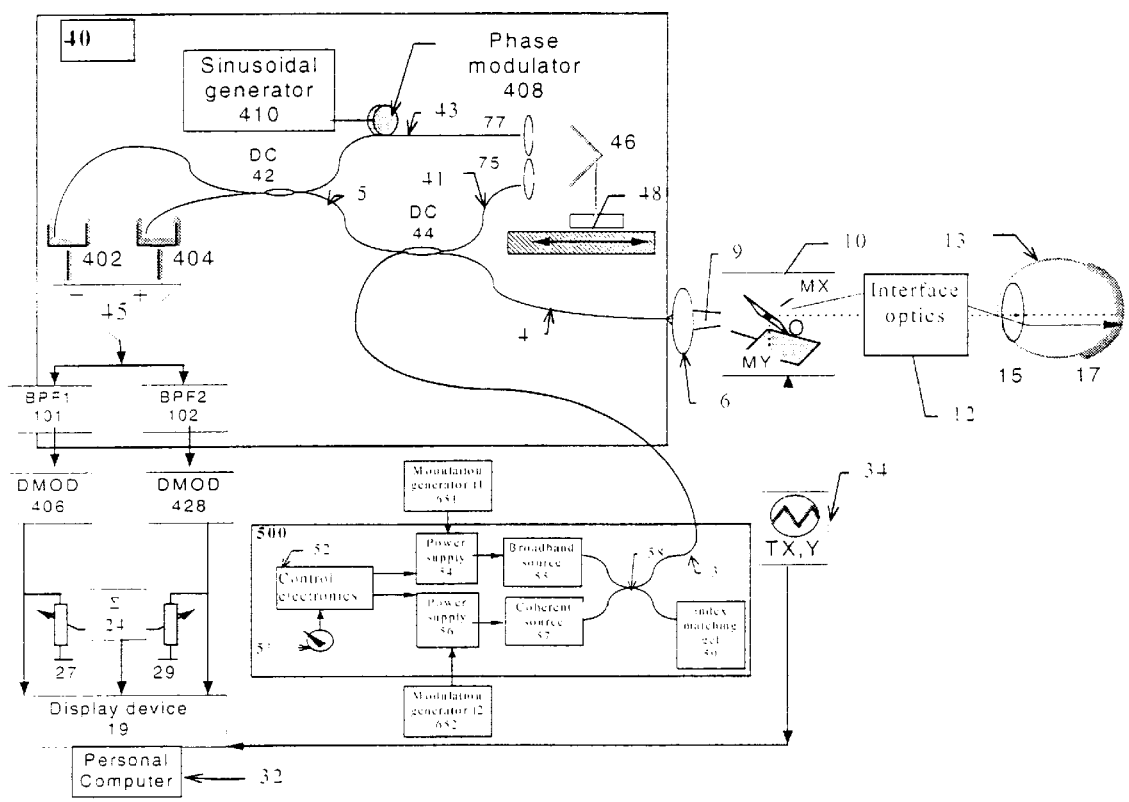
FIG. 9 shows an embodiment of a tomographic mapping apparatus with adjustable depth resolution, which uses a modified version of the source with adjustable coherence length shown in FIG. 8.

FIG. 9 diagrammatically shows an ophthalmic instrument according to the invention where the two images created by each of the sources used in FIGS. 8 are displayed simultaneously. To this end, the two sources in the said source with adjustable coherence length are modulated in intensity at two different frequencies, using the generators 651 and 652; and two band pass filters, 101 and 102 tuned on these two different frequencies are used to separate the signals, with the necessary image bandwidth.

The signals delivered by the two bandpass filters, are weighted by the potentiometers 27 and 29, respectively, at the inputs of a summator 24, the resultant signal being displayed and recorded by means of a suitable display device 19, such as a frame grabber, a storage oscilloscope or a suitable printer. The two signals are also applied to the device 19, which can display one or both of these signals, or the weighted combination under the computer 32 control.

Figure 10:
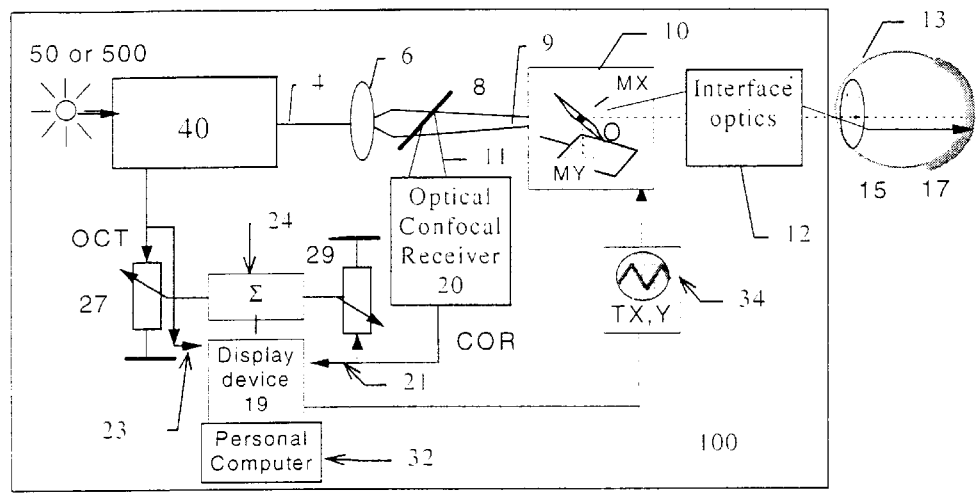
FIG. 10 shows a second embodiment of the present invention.

FIG. 10 diagrammatically shows an ophthalmic instrument according to a second embodiment of the present invention. As shown in FIG. 10, the apparatus 100 comprises an OCT interferometer 40 excited by a source which can be either broadband, 50, or with adjustable coherence length, 500. An OCT sample beam 4 is output from OCT interferometer 40, in fiber if the OCT interferometer is in fiber, or if it is in bulk, 4 is an optical output beam. The OCT sample beam output 4 is focused by an optical element 6, such as a refractive or reflective optical element, split by a beamsplitter 8 into a beam 9 which is then deflected by a 2D scanner head 10 to scan transversally, via interface optics 12, an object 13. In FIG. 10 the object 13 is an eye, the beam being focused by the eye lens 15 onto the retina 17. The light returned by the object, reflected and scattered, is partly collected via the focusing element 6 back into the path 4 and partly, a beam 11, collected by a confocal optical receiver (COR) 20. The signal delivered by the OCT, 23, and the signal delivered by COR at its output 21 are weighted by the potentiometers 27 and 29 respectively at the inputs of a summator 24, the resultant signal being displayed and recorded by means of a suitable display device 19, such as a frame grabber, a storage oscilloscope or a suitable printer. The device 19 is under computer 32 control. The signals of the OCT and COR are also applied to the device 19, which can display one or both of these signals under the computer 32 control. The images can be displayed in linear or logarithmic scale on grey or false colour coded format. When the OCT and COR images are to be displayed separately, a special device 19 with dual display capabilities is required.

Figure 11:
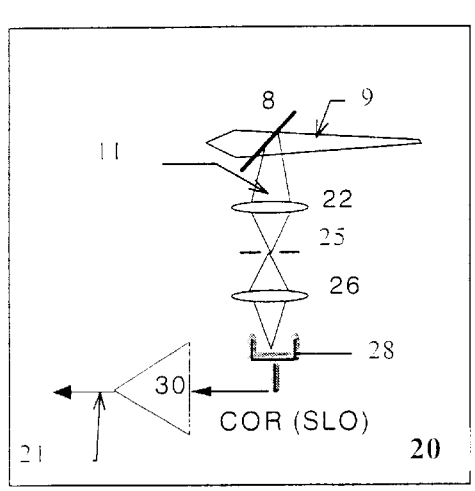
FIG. 11 shows an optical confocal receiver using a pinhole and lenses, with adjustable focal depth sectioning interval for use in the present invention.

FIG. 11 diagrammatically shows an embodiment of the confocal optical receiver 20 for the embodiment of the invention in FIG. 9, equipped with the lenses 22 and 26, a pinhole 25 being placed in the focal plane of the lenses 22 and 26, with the lens 26 removed when simpler implementation is acceptable. After passing through the lenses 22, 26 the light is collected by a photodetector 28. The photodetected current is amplified in an amplifier 30 and supplied to the input 21 of the display device 19. By modifying the pinhole 254, or the focal lengths of the lenses 22 and 26 and their distances to the pinhole 25, different depth sectioning intervals are obtained. A resolution of 300 $\mu$m is available for the COR when the object is the eye, in which case the confocal receiver 20, the splitter 8 along with the scanner head 10 and the interface optics 12 act as an SLO. When the aperture 25 is open at maximum, the image will look contiguous, not fragmented and the entire scene will occupy the display, with pixel-to-pixel correspondence with the OCT image. Consequently, when the embodiment of FIG. 10 is equipped with the confocal receiver of FIG. 11, three possibilities to adjust the depth sectioning interval exist. The first possibility consists in adjusting the depth sectioning interval of the COR image by means of devices in the COR which are independent of the source used either broadband 50 or adjustable coherence length 500. Such adjustment provides a depth sectioning interval adjustable from 300 $\mu$m upwards when the object 13 is the eye. A second possibility consists in varying the sectioning interval of the OCT image by changing the coherence length of the source 500; in this case, the depth sectioning interval on the OCT image can be adjusted from the minimum given by the minimum coherence length of the source 500, say 10 $\mu$m, up to the maximum coherence length of the source 500, say 300 $\mu$m, providing an adjustment interval on the OCT image which is complementary to the interval provided by the COR image. A third possibility consists in weighting the OCT and COR signals applied to the input of the summator 24 in FIG. 10, by means of potentiometers 27 and 29 when the optical source is broadband, 50. If the source used is the source with adjustable coherence length 500, a more diverse adjustment can be operated, actuating on both the sectioning interval of the OCT image and on the weighting of the OCT and COR signals.

Figure 12:
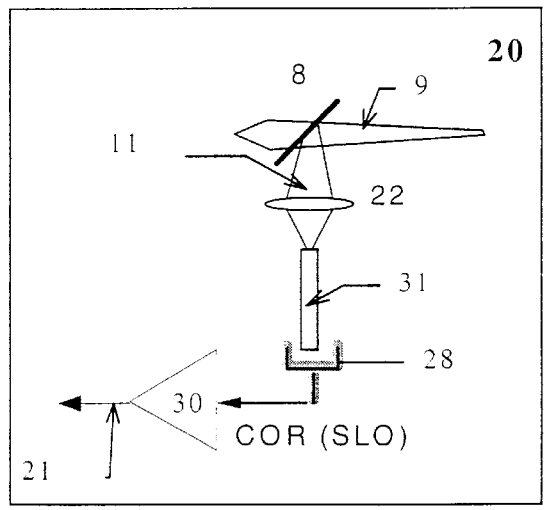
FIG. 12 shows a further optical confocal receiver for use in the present invention wherein a fiber is used as aperture in the receiver to ensure a small depth sectioning interval.

FIG. 12 diagrammatically shows another embodiment of an optical confocal receiver 20 for use in the embodiment of the invention of FIG. 9, where the aperture of a multimode or single mode fiber 31, pigtailed to a photodetector 28 is used to ensure a high confocal condition. In this case, the depth sectioning interval on the image displayed using the signal from the confocal optical receiver, COR, is not adjustable. For this embodiment, the sectioning depth interval in the final image can be adjusted only by weighting the OCT and COR signals applied to the input of the summator 24 in FIG. 10, by means of potentiometers 27 and 29 when a broadband source 50 is used. When the source with adjustable coherence length 500 is used, two procedures for adjusting the depth sectioning interval are possible: weighting the OCT and COR signals or adjusting the OCT depth sectioning interval by changing the coherence length of the source.

Figure 13:
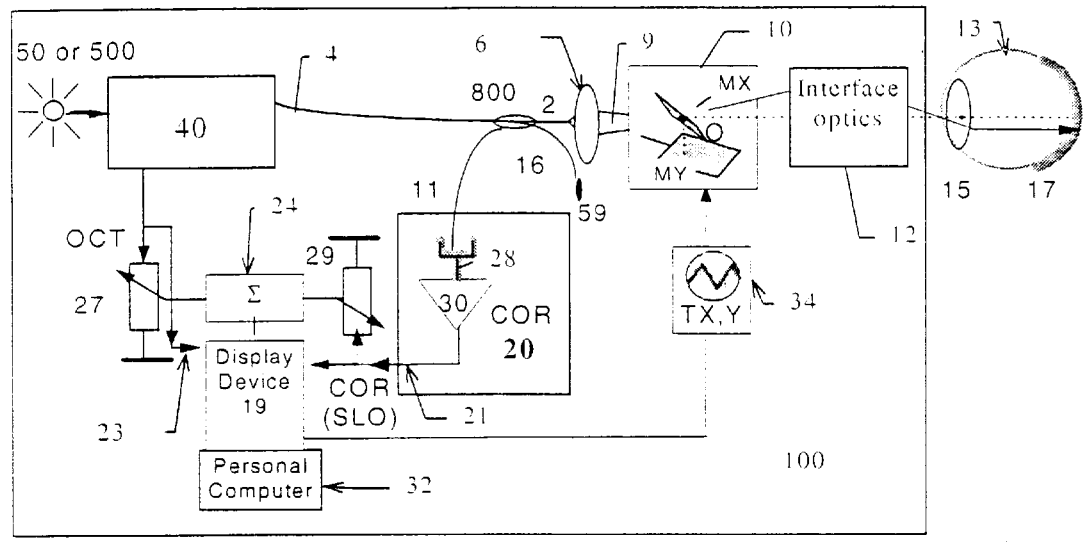
FIG. 13 shows a third embodiment of the present invention wherein a fiberized coupler is used as the said optical splitter.

FIG. 13 diagrammatically shows a third embodiment of the present invention, where the beamsplitter 8 is now replaced by a directional coupler 800 and the light returned from the object path, i.e.: from the object 13, via the interface optics 12, the scanner head 10 and focusing element 6 is sent to the confocal receiver 20 via the fiber 2 and fiber 11, the signal from the confocal optical receiver, COR, being obtained after photodetection in the pigtailed photodetector 28 and amplification by amplifier 30. Preferably, the fiber ends 2 and 16 are angle-cut and the fiber end 16 is placed in index matching gel 59 to reduce the amount of light from the OCT source being reflected towards the confocal receiver. For this embodiment, the depth sectioning interval on the image displayed using the signal COR is given by the numerical aperture of the fiber 2 and is not adjustable. The sectioning depth interval in the final image can be adjusted only by weighting the OCT and COR signals applied to the input of the summator 24, by means of potentiometers 27 and 29 when a broadband source 50 is used. When the source with adjustable coherence length 500 is used, two procedures for adjusting the depth sectioning interval are possible: weighting the OCT and COR signals or adjusting the OCT depth sectioning interval by changing the coherence length of the source.

Figure 14A:
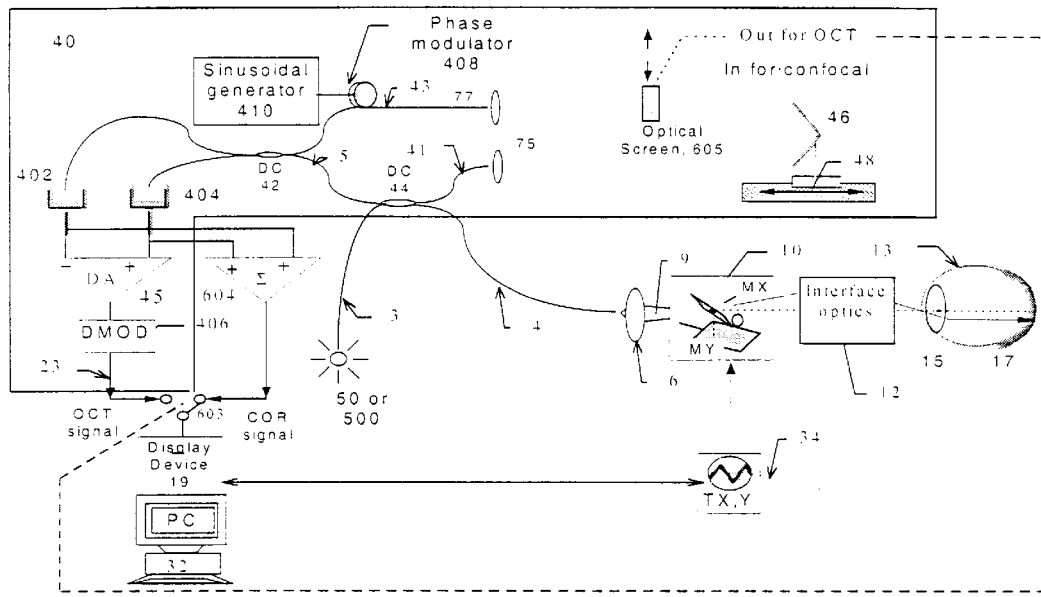
FIG. 14A shows another embodiment of a tomographic mapping apparatus with adjustable depth resolution using both optic fiber and bulk components which can sequentially provide two tomographic images with different sectioning intervals.

FIG. 14A shows, in diagrammatic form, a fourth embodiment of an (ophthalmic) apparatus 100 in accordance with the present invention, which can sequentially display two images of very different depth resolution. As shown in FIG. 14A, the apparatus 100 comprises a fiberized interferometer 40. Two regimes of operation are selectable: OCT and confocal by means of a switch, 603, which for the confocal regime, synchronously shifts an opaque screen, 605, into the reference beam of the interferometer, and larger amplification of the photodetected signal in the amplifier 604 is applied before being displayed by display device 19, such as a frame grabber, a storage oscilloscope or a suitable printer. When balance detection is used, as shown in FIG. 2A, the amplifier 604 has also the function of addition of the two photodetector signals instead of being subtracted as for the OCT regime. The display device 19 is under computer 32 control. In the confocal case, the fiber aperture acts as a confocal restricting aperture, which depending on the fiber used, determines a depth sectioning interval of 0.5–2 mm.

If the photodetectors 402 and 404 are avalanche, the photodetection gain is switched between a large value obtained in the regime of multiplication for the confocal case and a small value in the OCT case when the avalanche photodetectors have little or no multiplication, by simply blocking or unblocking the reference power, the consequent voltage drop on the resistor in series with the avalanche photodetector when large optical power is applied acting as a gain control.

Figure 14B:
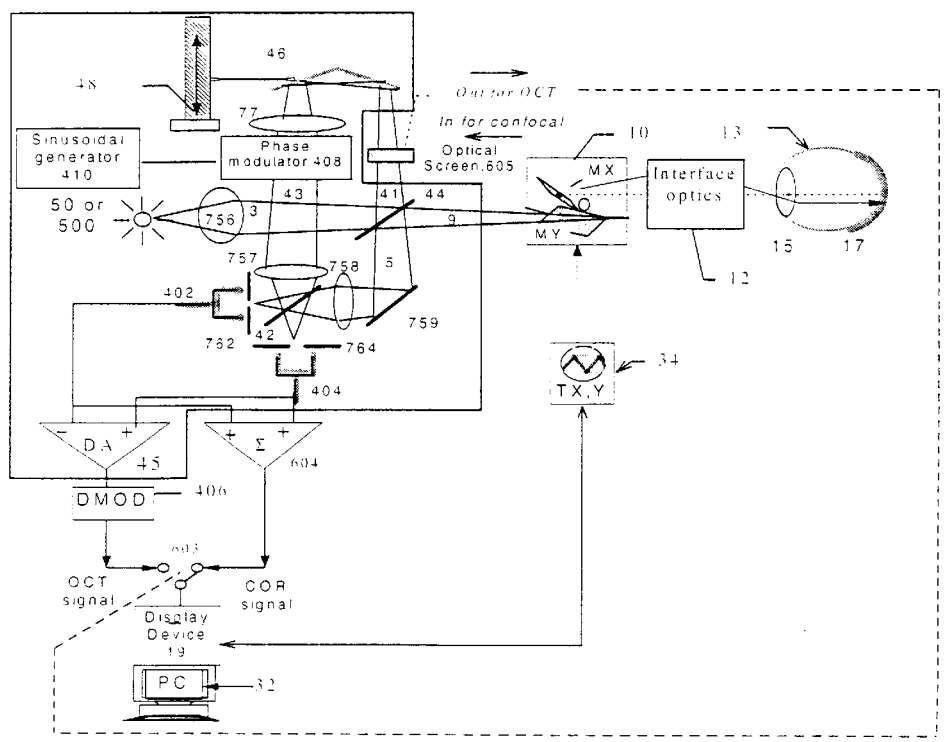
FIG. 14B shows another embodiment of a tomographic mapping apparatus with adjustable depth resolution using only bulk components which can sequentially provide tomographic images with two different sectioning intervals, and for at least one of the images being possible to adjust the depth resolution.

FIG. 14B shows, in diagrammatic form, another embodiment of an (ophthalmic) apparatus 100 in accordance with the present invention, which can sequentially display two images of very different depth resolution, one image admitting adjustment of the depth resolution. As shown in FIG.

14B, the apparatus 100 comprises a bulk interferometer 40, equipped with synchronous adjustable pinholes 762 and 764 or synchronous adjustable focusing elements 757 and 758 to alter the numerical aperture of the receiving photodetectors 402 and 404. Two regimes of operation are selectable: OCT and confocal by means of a switch 603, which for the confocal regime, synchronously shifts an opaque screen, 605 into the reference beam, and larger amplification of the photodetected signal in the amplifier 604 is applied before the being displayed by display device 19, such as a frame grabber, a storage oscilloscope or a suitable printer. When balance detection is used, as shown in FIG. 14B, the amplifier 604 has also the function of adding the two photodetector signals instead of being subtracted as for the OCT regime. The display device 19 is under computer 32 control. In the confocal case, the depth resolution is adjustable by varying simultaneously the numerical apertures of the two collecting optics, either the pinholes 762, 764 or focusing elements 757 and 758, which when imaging the eye, could cover a range, from 300 μm upwards. Obviously, in FIGS. 14A and 14B, the depth resolution can be made adjustable by means of the source 500 with adjustable coherence length, as described above.

Figure 15:
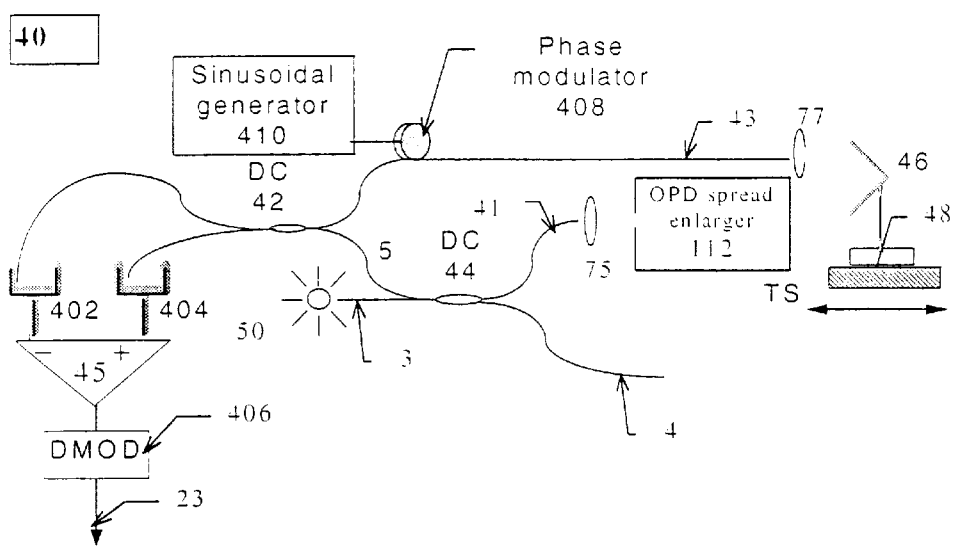
FIG. 15 shows a fourth embodiment of an optical coherence tomography mapping apparatus for use in the present invention.

FIG. 15 diagrammatically shows a fifth embodiment of an optical mapping apparatus with adjustable depth resolution, where an optical element 112 is introduced in the object or reference path of the OCT interferometer 40, with the effect of enlarging the correlation profile of the source. In the paper "Dispersion effects in partial coherence interferometry" by Ch. K. Hitzenberger, W. Drexler, A. Baumgartner and A. F. Fercher, published in the proceedings SPIE 2981, (1997), pp. 29–36, the dispersion effect is studied from the negative perspective which leads to enlargement of the correlation function of the optical field. In FIG. 15, it is the same phenomenon of dispersion which is used effectively to increase the size of the fragments sampled by the OCT from the target, this increase is due to an equivalent enlargement of the correlation function of the broadband optical source when measured with an interferometer with an OPD about zero. The element 112 acts as an OPD spread enlarger. This element is a dispersive element, a diffractive element, or a special device, as shown in FIG. 16 and FIG. 17, respectively. In previous papers, the arrangement in FIG. 16 was used to compensate for dispersion when the coherence length of the source was less than 30 μm. In our invention, the dispersive element is used to increase dispersion controllably, to such an extent as to increase the depth sectioning interval of the instrument over 100 μm. The OPD spread enlarger 112 is based on known variable dispersion means. The higher the dispersion, the higher the enlargement of the coherence length. An enlargement of up to 300 μm is possible using high dispersion materials, as for instance 2.07 μmm ZnSe increases the coherence length of a laser $TiAl_2O_3$ from 2.1 μm to 268 μm.

The OPD spread enlarger element described in FIG. 16 uses two prisms 122 and 124 of convenient width and index of refraction. Adjusting the length of path in glass, the depth sectioning interval of the instrument 100 can be adjusted. This element can be placed in either the object or the reference path. In FIG. 15, the element 112 is placed in the reference path between the fiber 41 and the reference assembly 46. If the OCT interferometer 40 is in bulk, the lens 75 can be removed.

The OPD spread enlarger element shown in FIG. 17, uses a number of very thin parallel glass plates, (nine are shown in FIG. 17), between two lenses 75 and 136. The element in FIG. 17 can also be implemented by means of integrated optics. Using two lenses as shown, such a system can be placed in a section of fiber. For bulk interferometer implementation of the OCT 40, the lenses 134 and 136 can be removed. The device shown in FIG. 17 provides 9 different beams with increasing optical paths, spreading the OPD profile of the source correlation function. The power of each delayed beam is proportional with the integral of the power distribution in the beam over the area of the respective plate. In order to ensure that all 9 beams have the same power, the width sampled by the beam out of each plate is weighted with an inverse proportional law to the power distribution within the cross sectional area of the beam.

U.S. Pat. No. 5,268,738 utilizes a number of multiple delayed copies to increase the OCT range. The delay between the adjacent copies is much larger than the coherence length of the source, and each copy is individually modulated and then demodulated. As opposed to this, the present invention uses the multiple copies for the enlargement of the correlation profile and all the images created by the delayed copies are superimposed. The delay, given by the thickness of each plate multiplied by the index of refraction, must be less than half of the coherence length. The higher the number of plates, the smoother the profile of the correlation function governing the OCT operation becomes. By designing the width of each plate intercepting the beam in relation with the position of the plate in the enlarged beam between the lenses 75 and 136 in FIG. 17, an overall Gaussian profile for the correlation function can be obtained, which can simulate the resolution profile in depth of an SLO with the same equivalent depth width.

FIG. 18 diagrammatically shows a sixth embodiment of optical apparatus for mapping objects with adjustable depth resolution 100 according to the present invention. The apparatus 100 comprises a different OCT, where 2 interferometers are shown for simplicity. More interferometers could be installed, if desired. The fiber path 5 is split into two and two more couplers 434 and 422 are introduced. The object path of the first interferometer is via the fiber 33, coupler 434, fiber 5, coupler 44 to the fiber 4, scanner 10 and object 13 and then returns back via the same elements to the coupler 42. The reference path is via the coupler 44, element 75, assembly 46, element 77, fiber 43 and coupler 42 with the interference signal processed by the photodetectors 402 and 404. The second interferometer has its object path via the fiber 35, coupler 434, and then shares the same elements with the first interferometer object path. The reference path of the second interferometer uses the reflector 454 and the beamsplitter 452, supported by the assembly 432 which is mounted along with the assembly 46 on the same device 48 for longitudinal scanning, the OPD enlarger 112, beam 45, and the interference signal processed by the photodetectors 424 and 426. Alternatively, the two reference paths can be simultaneously scanned using a fiber wrapped around piezocylinder placed in the common path of both reference paths, i.e.: along the fiber 43, in which case the position of elements 46 and 432 are adjusted to equalize the reference paths and device 48 is removed. Any other device for longitudinal scanning such as described in relation to the OCT in FIG. 1, can be used. The OPD spread enlarger 112 can be implemented using either of those shown in FIGS. 16 or 17 or using a diffractive element. The two reference paths, one including the fiber 41, assembly 46, fiber 43 and the other including fiber 41, beamsplitter 452, mirror 454, OPD spread enlarger 112 and path 45 are substantially equal, when the lengths of the fibers 33 and 35 connecting the coupler 434 to the couplers 42 and 422 are also equal. Any substantial differences in the fiber lengths of the coupler 434 can be compensated for in either of the paths 41, 43 or 45 in order to ensure coherence matching and keeping dispersion low in the first interferometer. On the other hand, it would be desirable to have the air path 45 short, to help with the dispersion in the second interferometer. The demodulator 406 processes the signal from the first interferometer, which provides the image with the best depth resolution out of all the other interferometers, and drives the input 23 of the display device 19 while the demodulator 428 processes the signal with the larger sectioning interval provided by the second interferometer and drives the input 21 of the display device 19. Practically, this embodiment of the optical mapping apparatus with adjustable depth resolution replaces the COR channel in the embodiment in FIG. 10 with an OCT channel of similar depth resolution, as obtained in the second interferometer in FIG. 18. The display device 19 is equipped with means to display the two images separately or/and to display pixel-by-pixel a combination of the two images in a single image.

The schematic diagram in FIG. 18 can be extended to include more interferometers, for instance by extending the coupler 434 from 1:2 to 1: n, and devising a bulk equivalent splitter for the assemblies 432 and 46 to divide the reference beam output of fiber 41 into n reference beams, with all the reference paths adjusted simultaneously by shifting the translation stage 48 and with n-1 interferometers, containing different OPD enlarger elements, creating correspondingly images with different depth sectioning widths.

Figure 19:
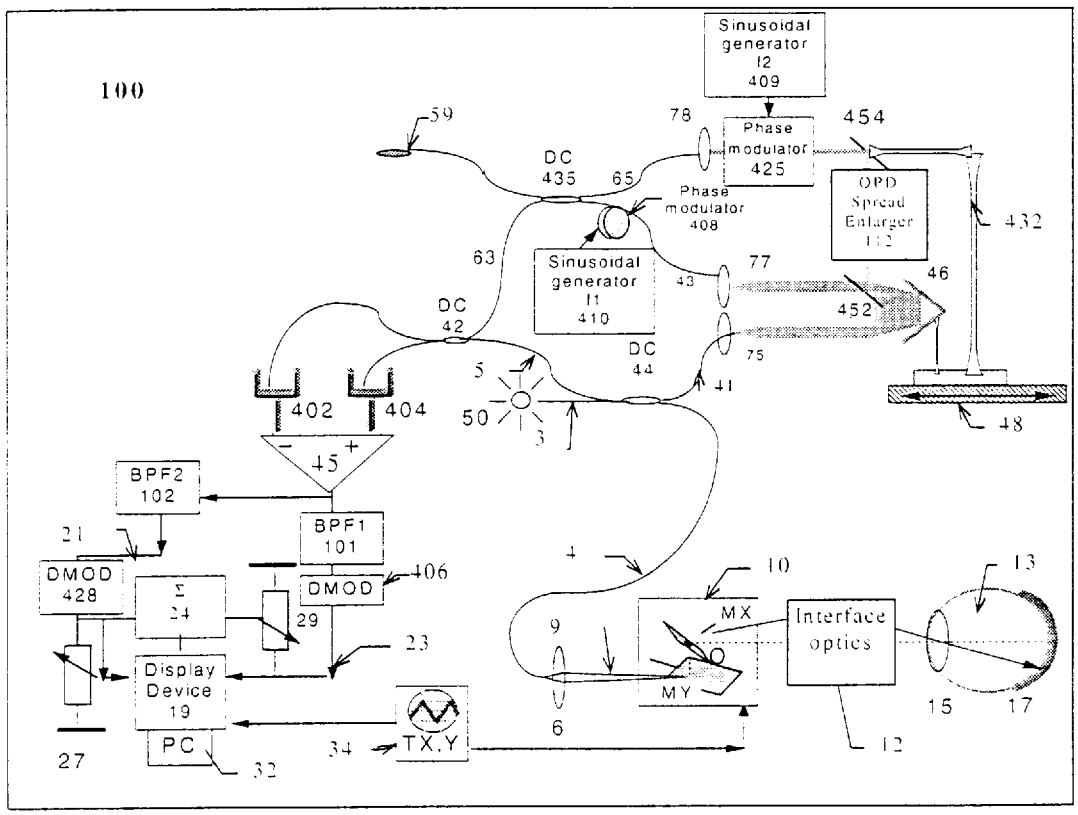
FIG. 19 shows another embodiment of the present invention.

FIG. 19 diagrammatically shows a seventh embodiment of an optical apparatus for mapping objects with adjustable depth resolution 100 in accordance with the present invention. The apparatus 100 comprises a different OCT where 2 interferometers are shown for simplicity. More interferometers could be installed if desired with the requirement that the two (or all the) interferometers have the same object path. The object path is via the fiber 5, coupler 44 to the fiber 4, scanner 10 and object 13 and then returns back via the same elements to the coupler 42. The two reference paths have in common the fiber 41, element 75, assembly 46, and the beamsplitter 452 and the output fiber 63 of the coupler 435. After the beamsplitter 452, supported by the assembly 432, the nondispersive reference path continues via element 77, fiber 43, phase modulator 408 to coupler 435, with the cumulated glass length substantially equal with the glass length in the object path. The second reference path, which is dispersive, continues via the OPD spread enlarger 112, mirror 454 supported by the assembly 432, phase modulator 425, element 78 and fiber 65 to the coupler 435. The phase modulator 425 is driven by the sinusoidal generator 409 at a frequency f2, much larger than f1+double the image bandwidth, where f1 is the frequency of the sinusoidal generator 410 driving the modulator 408 in the nondispersive reference path. The phase modulator 425 uses an electro-optic, or an acousto-optic or a magneto-optic modulator, or a fiberized modulator which is mounted on the fiber 65. Similarly, the phase modulator 408, can be equally implemented in bulk using an electro-optic, acousto-optic or a magneto-optic modulator, in which case it is mounted between the beamsplitter 452 and the element 77. The assembly 432 is mounted along with the assembly 46 on the same device 48 for longitudinal scanning. Alternatively, the two reference paths can be simultaneously scanned using a fiber wrapped around piezo-cylinder placed in the common path of both reference paths, i.e.: along the fiber 41 or 63, in which case the position of elements 46 and 432 are adjusted to equalize the reference paths and device 48 is removed. Any other device for longitudinal scanning such as described in relation to the OCT in FIG. 1 can be used. The OPD spread enlarger 112 can be implemented using either of the embodiments shown in FIGS. 16 or 17 or using a diffractive element. The other fiber end of the coupler 435 is terminated in the index matching gel 59 to avoid reflection from it. The two reference optical paths are substantially equal. Any substantial differences in the fiber lengths of the coupler 435 can be compensated for in the paths 41 in order to ensure coherence matching and minimising dispersion in the nondispersive interferometer. On the other hand, it would be desirable to have 41 and 43 short and 65 longer, to help with the dispersion in the second (dispersive) interferometer.

The signal due to the interference along the first reference path is filtered by the bandpass filter 101 tuned on the frequency f1 or its multiples. The signal due to the interference along the second reference path is filtered by the bandpass filter 102 tuned on the frequency f2 or its multiples. The demodulator 406 processes the signal from the first interferometer, which provides the image with the best depth resolution out of the two interferometers, and drives the input 23 of the display device 19. The demodulator 428 processes the signal with the larger sectioning interval provided by the dispersive interferometer and drives the input 21 of the display device 19. Practically, this embodiment of the optical mapping apparatus with adjustable depth resolution replaces the COR channel in the embodiment in FIG. 10 with an OCT channel of similar depth resolution, as obtained in the dispersive interferometer in FIG. 19. The display device 19 is equipped with means to display the two images separately or/and to display pixel by pixel a combination of the two images in a single image. This embodiment has the advantage that it does not divide the object signal prior to the receiving coupler 42, as the coupler 434 does in FIG. 18.

The schematic diagram in FIG. 19 can be extended to include more interferometers, for instance by extending the coupler 435 from a 1:2 to a 1: n coupler, and devising a bulk equivalent splitter for the assemblies 432 and 46 to divide the reference beam output of fiber 41 into n reference beams, with all the reference paths adjusted simultaneously by shifting the translation stage 48 and with each interferometer containing a phase modulator and a different OPD enlarger element to create each an image with a different depth sectioning width.

Figure 20:
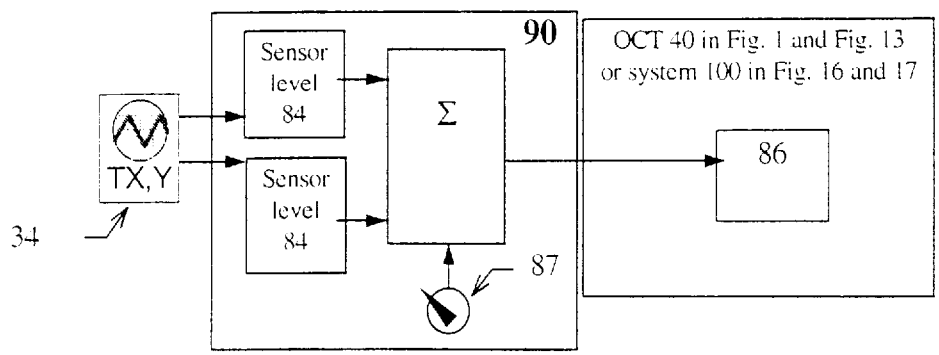
FIG. 20 shows a feedback loop for use in the present invention.

FIG. 20 shows an embodiment of another aspect of the invention. This embodiment permits the planarization or bending of the wavefront at the back of the eye lens. This is obtained by a synchronous control of the OPD in the OCT interferometer in any of the implementations above as shown in FIG. 1, FIG. 2, FIG. 10, FIG. 14A, FIG. 14B, FIG. 15, FIG. 18, or FIG. 19, by means of feedback directed by the raster scanning means. For each direction towards which the beam is pointed, the controlling feedback block 90 applies a control signal onto an optical delay element 86 in the reference or object path of the OCT. The larger the angle at which the ray enters the eye, the larger the object path length. Each direction is given by two voltages applied by the generator 34 to the two transversal scanners 12. The two blocks 84 sense the level of these voltages and output a commensurate voltage. The adder 85 provides the control signal to the optical delay device 86, which could be a sufficient long fiber wrapped around piezo-cylinders. Equivalently, the device 86 can be built using vibrators, as for instance two loudspeakers can shift the two mirror parts of the reflecting element 46 in FIG. 1 and FIGS. 9, 14A, 14B, or 15, along directions at 45° in relation to the axes of the elements 75 and 77. The device 86 can also be built using a galvanometer scanner in association with a grating as disclosed in the paper "In vivo endoscopic optical biopsy with optical coherence tomography", by G. J. Tearney, M. E. Brezinski, B. E. Bouma, S. A. Boppart, C. Pitris, J. F. Southern and J. G. Fujimoto, published in Science, vol. 276, (1997), pp. 2037–2039. Another possibility is to use a galvanometer scanner in association with lenses and mirrors as shown in the present invention in FIG. 21 and 22 or two galvanometer scanners in association with lenses as shown in FIG. 23. The device 86, depending on implementation, can be interleaved in any of the fibers 4, 5, 41, or 43 in FIG. 1A, FIG. 14A, FIG. 15 or in the fiber paths 4, 5, and 41 only in FIG. 18 or in the fiber 5, 41, and 63 only in FIG. 19, or in the path 4, 9, 41, or 43 in FIG. 1B, FIG. 14B or in the equivalent path of the fiber paths when the configurations in FIG. 18 and 19 are translated in bulk. The device 86 works at twice the line frequency value, so at twice the frequency of the sawtooth signal applied to the transversal scanner which gives the line in the final image raster. Typically, this means about 1 kHz. The amplitude of the path change introduced by the device 86 should be at least a few hundred microns. The wavefront curvature could be undercorrected, corrected or overcorrected modifying the gain of the summator 85 via the knob 87. For a good correction, i.e.: when the wavefront is plane, the focal length of the eye lens should be known.

Alternatively, the two sensor level elements 84 can be electrical circuits with memories programmed to output a certain voltage for a given input level.

Figure 21:
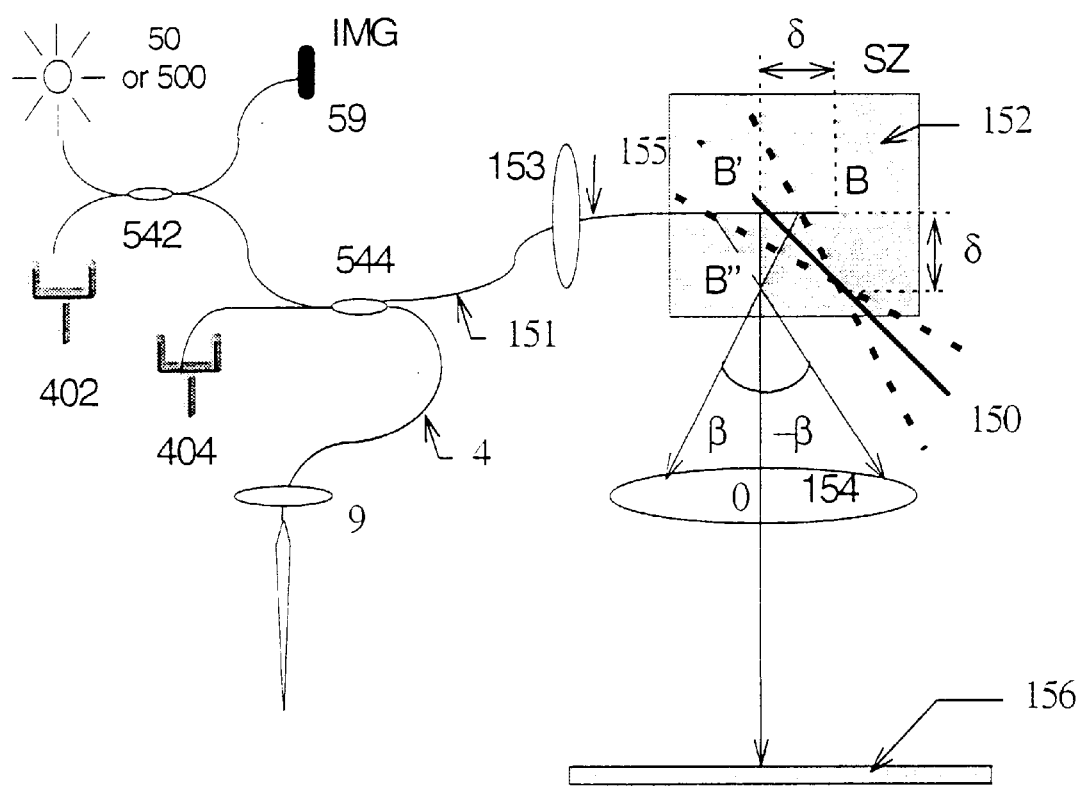
FIG. 21 shows a longitudinal scanning for use in the invention.

FIG. 21 shows an embodiment scanner to create a fast a means which uses a galvoscanner to create a fast and low dispersive variation of the optical path. The configuration of 50:50 couplers 544 and 542 is used to implement balance detection. The channel supplied by the photodetector 402 needs twice as much gain as the channel supplied by the photodetector 404.

Consideration will now be given to the case when the interferometer is matched, i.e.: the OPD=0 and the reference beam 155 falls on a point on the galvanometer-mirror 150 away by a quantity δ from the axis of rotation, when the galvo-scanner 152 is moved to the lens 154 by the same quantity (equivalent results are obtained if the beam falls on the galvo-scanner 152 at −δ). The rays are deflected by the galvanometer-mirror 150, refracted by the lens 154, reflected by the mirror 156 perpendicularly oriented to the optical axis in the focal plane of lens 154, refracted by the lens 154 again and retraced along the original path back to the beam 155 and to the fiber 151 via the focusing element 153. For small scanning angles β, due to a rotation of the β/2 of the galvanometer-mirror, the path imbalance P introduced between the central ray (along the optic axis) and the ray deflected by an angle β from the optic axis after being reflected from the mirror 154 is given by equation:

$$P = 2\delta\beta \quad (1)$$

For each variation of P by λ, a period of the photodetected beating signal results due to scanning the mirror 156. The frequency of this signal for a triangular driving signal is given approximately by:

$$v = \frac{8kF_zV_z}{\lambda}\delta \quad (2)$$

where k is the scanner sensitivity, $V_z$ the amplitude and $F_z$ the frequency of the triangular wave applied to scanner 152. For a ramp signal, the equation (2) should be divided by 2.

In FIG. 21, the shift δ was obtained by placing the galvo-scanner 152 closer to the lens 154, in which case the point of incidence, B, of the beam on the galvanometer-mirror is shifted towards the collimator 153, to a point B', by the same amount. The apparent point, B", origin of the fan of the rays deflected is situated on the axis of the lens 154. (If the scanner 152 is moved away from the lens 154, B" moves in the same direction by about the same distance).

To ensure a telecentric set-up, the distance lens 154 to the mirror 156 and to the point B" is equal with the focal length of the lens 154.

In this way, the direction of the returned beam is brought parallel to the direction of emergent beam 155 from the lens 153. This arrangement minimizes the parasitic intensity modulation owing to the variation in the light reinjected into the fiber while 150 is driven.

Figure 22:
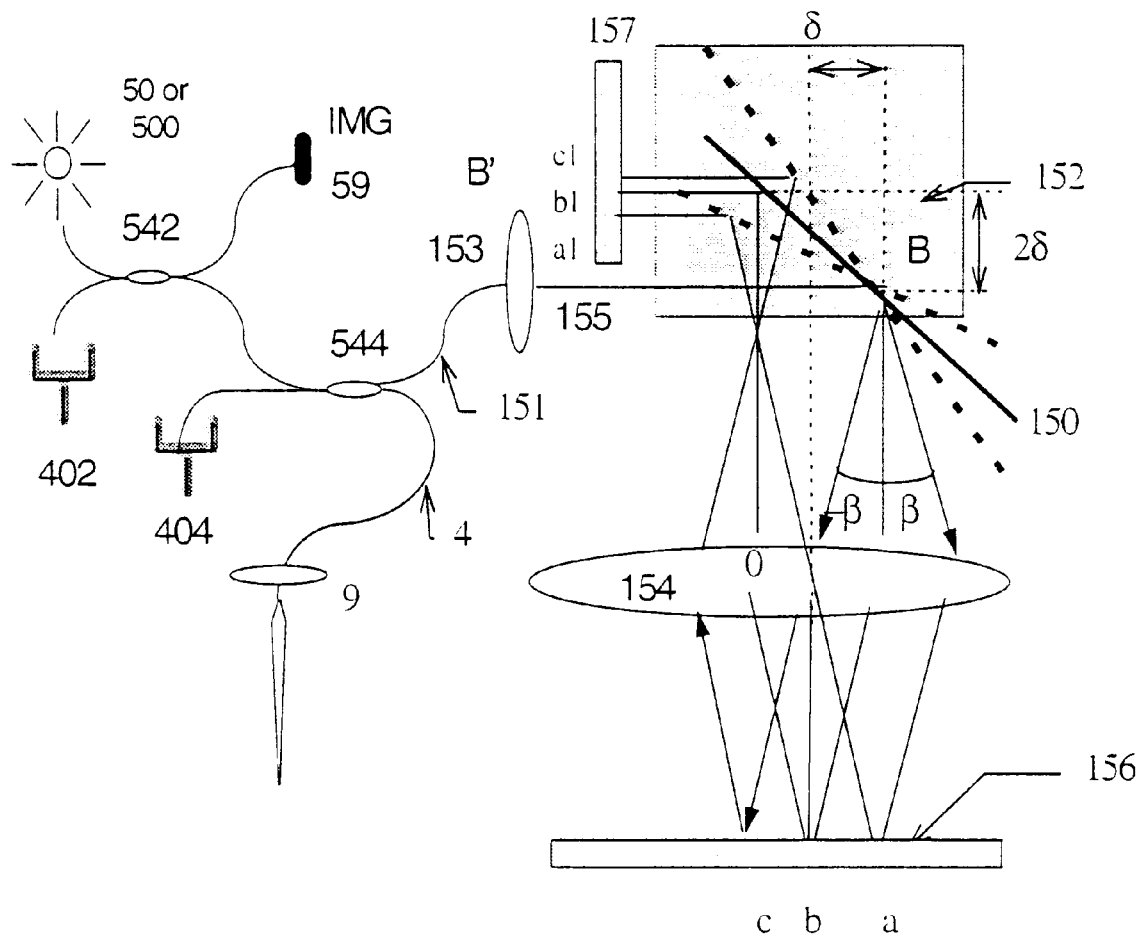
FIG. 22 shows a further longitudinal scanning device for use in the invention.
Figure 23:
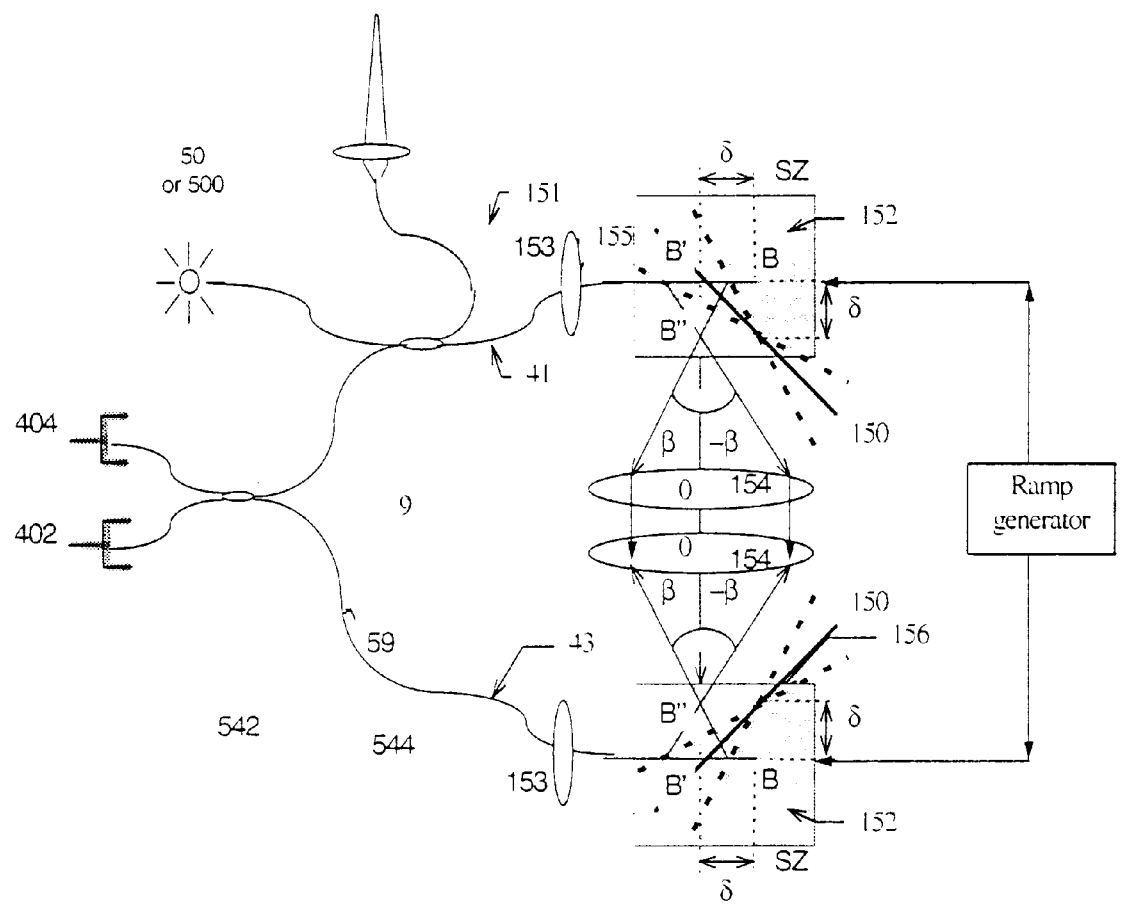
FIG. 23 shows a further longitudinal scanning device for use in the invention where the incoming direction of the beam is different from its outcome direction.

A second embodiment of a low dispersion device for longitudinal fast path variation is shown in FIG. 22. In this case the beam 155 falls in the point B, on the axis of rotation of the mirror 150. The path imbalance variation is created by shifting the lens 154 laterally from the optical axis crossing the point B, by a quantity δ. After crossing the lens 154, the beam is reflected from the mirror 156 in the points a (β_ray), b (0 ray) and c (−β ray) and returns to a parallel direction to the incident beam 155 and is incident on a second mirror 157 in the respective points a1, b1 and c1. After the reflection on the galvanometer-mirror 150, it goes back to the lens 154, mirror 156, point B on the galvanometer-mirror 150 and finally along the incident beam 155 back to the fiber 151. For simplicity, the drawing in FIG. 22 corresponds to the case when the angle β_has such a value that the point b coincides with the axis of the lens 154.

A third embodiment of a low dispersion device for longitudinal fast path variation is shown in FIG. 23, which uses two systems in FIG. 21 in order to redirect the deflected light to a different fiber (path), useful for the OCTs with balance detection and recirculation of the reference power.

Any of the OCT systems described so far can be used to build longitudinal OCT images. In this case, the transversal scanning system 10 is operated along one direction, X or Y, or is controlled to sample an inclined line, or a circular or elliptical shape. After each such transversal complete cycle, the reference path is stepped or during each such transversal complete cycle the reference path is changed at much smaller speed than the transversal scanning speed, using any devices known in the art to alter the path or one of the embodiments in FIGS. 21, 22, or 23. A 2D map is obtained, with one coordinate the depth, explored using the systems for longitudinal scanning and the other transversal, given by the transversal scanner head.

For the embodiments in FIGS. 21 and 23, when used to produce longitudinal OCT images, the regime of operation of the vertical display of the device 19 in FIGS. 2, 9, 10, 13, 14A, 14B, 18 and 19 is controlled by the slope of the ramp signal driving the galvo-scanner 152. At every change in the above mentioned slope, the sense of the raster scan in the final displayed frame along the depth direction is changed, i.e.: the voltage applied to the vertical or horizontal plates of the CRT has a triangular shape as different from the sawtooth shape commonly used in TVs and PCs CRTs.

Alternatively, the operation of changing the order of display and of storing can also be implemented electronically in digital format in the display device (frame grabber for instance). In this way, irrespective of the sense of longitudinal scan, the depth axis sense of the image displayed does not change during the longitudinal scan.

The equations (1) and (2) are equally applicable for galvanometer scanners used for the transversal scanning in OCT systems. In this case, equation (2) gives the frequency of the phase modulation, resulting from scanning a plane target. This "carrier" frequency can be used to carry the image bandwidth with no extra device acting as a phase modulator. The larger the δ, the higher the frequency of the carrier. In this way, the more the beam is shifted away from the galvanometer mirror, the larger the bandwidth of the signal which can be carried by the carrier.

This carrier appears from scanning the optical beam at coherence over the sampling function in the shape of a grid projected over the target. However, any tilts of the target will result in disturbing the value of the carrier. In other words, the sampling function is not constant over the target, i.e.: the transversal pixel size varies across the target.

Consequently, when the phase modulation due to the transversal scanner is employed, the band pass filter of the demodulation block has to allow for the variation of the carrier frequency due to the object tilts, roughness and profile, as shown in the paper: "En-face Coherence Imaging Using Galvanometer Scanner Modulation" by A. Gh. Podoleanu, G. M. Dobre, D. A. Jackson, Opt. Lett. 23, pp. 147–149, 1998. This is also valid when the optical beam is centred on the galvanometer mirror. In this case, as the sampling function looks in the form of Newton rings, the features in the centre of the rings will be sampled with a large periodicity, giving rise to carrier frequencies of low frequencies. If the bandwidth used skips 0 Hz and some of the low frequency components (in order to reject the 1/f noise), this would mean that the target parts not well sampled will be missed in the final image. For this reason, a combination of the modulation introduced by the galvanometer scanner when the beam is centred and the modulation introduced by a phase modulator should be employed, as explained in the paper "Transversal and Longitudinal Images from the Retina of the Living Eye Using Low Coherence Reflectometry", by A. Gh. Podoleanu, Mauritius Seeger, George M. Dobre, David J Webb, David A. Jackson, and F. Fitzke, Journal of Biomedical Optics, (1998), 3 (1), pp. 12–20. The frequency of the signal driving the phase modulator should be placed in the middle of the spectrum generated by the OCT when scanning the object transversally. Such a combination should also be employed when the size of the image is too small (for the human retina, this means about 0.5 mm transversal), in which case the carrier frequency is less than the bandwidth to be processed.

The transversal OCT images collected at different depths can be software processed to produce an equivalent transversal image, which can take the appearance of a superposed OCT images, or the appearance of the SLO image or of an image sampled out from the volume of the target using a conveniently shaped depth profile.

After collecting N images for N values of the path imbalance between the first and the second paths in the said interferometers, such an $O_s$ image can be obtained via the equation:

$$O_s(z) = \sum_{p=1}^{\infty} [O_{OCT}]_p^n C_p \quad (3)$$

The power n=1 and all the coefficients $C_p$=1 means simple superposition. The power n=2 means that an equivalent confocal image can be obtained when the coefficients C follows the depth sectioning profile of a confocal microscope. For instance, an image equivalent with the image produced by a state of the art SLO can be generated by using as coefficients C sampled values of its experimental depth sectioning profile.

An immediate advantage follows, such software generated profile will not have the adjacent satellite peaks characterising the experimental profiles.

Other equivalent images can be generated for larger values n.

Using a block which produces the squared version of the coherence signal, i.e., for n=2, an equivalent confocal image could be produced for each OCT image.

In any optical mapping apparatus of the present invention, a feedback loop under synchronous control of the raster scanning means for providing a curvature-transversal corrected image may be employed.

Moreover, in any optical mapping apparatus according to the present invention, the means to alter the length of the reference beam comprises at least one galvanometer-mirror, as noted above. Moreover, such means to alter the length of a reference beam for the interferometer may comprise a galvanometer-mirror placed at a distance f+δ from a convergent lens, and a mirror at a distance f from the convergent lens, where f is the focal length of the convergent lens and where the incidence beam on the galvanometer-mirror is δ away from the galvanometer-mirror axis.

The means to alter the length of a reference beam from an interferometer may likewise comprise a galvanometer-mirror, a convergent lens, and a first mirror at distance f away from the lens, together with a second mirror to implement a double pass on the galvanometer-mirror and so as to increase the path variation. Here, the point of incidence of a beam on the galvanometer-mirror is on its axis and in the focal plane of the lens; and the lens is laterally shifted in the plane of the scanned rays to ensure that, at the maximum angle of deviation, light reflected by the first mirror and reflected by the lens falls on the galvanometer-mirror.

Still further, the means to alter the length of the reference beam for the interferometer may comprise a first and second galvonmeter-mirror and respective first and second convergent lenses. Each converged lens is placed a distance f+s from its respective galvonmeter-mirror. The incidence beam on the first galvonmeter-mirror is redirected to the second galvonmeter-mirror, and thence to a second optical output path.

Optical mapping apparatus according to the present invention can be used to generate longitudinal images by using the transversal scanning means to general a 1 D sample over the object, and by replacing one of the transversal co-ordinates in the image with the longitudinal co-ordinate which corresponds to the optical path difference introduced by the longitudinal scanning means.

Still further, the apparatus may comprise a display scanning device in which a vertical display performs in alternate directions which are changed at each change of a voltage ramp slope of a voltage applied to a galvanometer-mirror.

Where a galvanometer scanner is employed, the line in the raster can be such that it can be used only to create the phase modulation necessary to carry parts of the OCT image signal.

Still further, a combination of the modulation due to the galvanometer scanner giving the line in the raster, and of the modulation due to an extra phase modulator, may be employed to carry all of the OCT image signal.

Moreover, an electronic filter may be employed in a receiver such that parts of the low frequency spectrum may be discarded. Frequencies up to the maximum phase modulation frequencies will, however, be passed, in keeping with the pass modulation introduced by transversal scanning of the object.

Still further, the frequency of the carrier created by the galvanometer scanner can be increased by shifting the incident optical beam away from the centre of the galvanometer mirror.

Optical mapping apparatus, in keeping with the present invention, can include software which will generate a transversal image Os, with different equivalent depth resolutions. Here, transversal OCT images are combined, which have been collected at different depths. The software generated image has a depth resolution between the minimum ensured by the coherence length of the optical source, and up to a maximum determined by the range of transversal images which have been collected. Each image contribution to the final image is weighted according to a predetermined profile.

Still further, a processor can be introduced into each input of a display device utilized in keeping with the present invention, so as to provide either a linear, logarithmic, or squared version of an input signal thereto.

The foregoing description has been presented for the sake of illustration and description only. As such, it is not intended to be exhaustive or to limit the invention to the precise form disclosed. For example, modifications and variations are possible in light of the above teaching which are considered to be within the scope of the present invention. Thus, it is to be understood that the claims appended hereto are intended to cover all such modifications and variations which fall within the true scope of the invention.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps. Moreover, use of the word "substantial" and "substantially", when used with an adjective or adverb, is intended to enhance the scope of the particular characteristic. For example, "substantially equal" means equal, or nearly equal, and/or exhibiting characteristics associated with apparent equality.

What is claimed is:

1. Optical mapping apparatus with adjustable depth resolution, comprising:

an interferometer chosen from the group consisting of fiberized interferometers and bulk interferometers, wherein said interferometer is excited by an optical source with adjustable coherence length, said interferometer comprising a first optical path and a second optical path leading to an object location, and to a reference reflector, respectively;

raster scanning means for transversally scanning an optical output from the said interferometer over a predetermined area about a point in a raster, or for moving the optical output from the interferometer to a point in a raster;

interface optics for transferring an optical beam from the raster scanning means to an object situated at the object location and for transferring an optical output beam reflected and scattered from the object back to the interferometer, along said first optical path;

means to alter at least one of the first optical path and the second path, so as to introduce intensity modulation, or phase modulation, or intensity modulation and phase modulation;

analyzing means, coupled to said raster scanning means, for demodulating the photodetected signal;

means for longitudinal scanning, to alter the length of the first optical path or the second optical path over a predetermined amount, for at least one of the points in the raster, in steps or continuously, at a pace synchronised with transversal scanning means; and means for displaying or storing an image of at least part of said object.

2. Optical mapping apparatus according to claim 1, wherein said optical source comprises two superposed radiation sources, one first said source having a very short coherence length, and the other second said source having a coherence length greater than that of the first said first source;

wherein both sources have substantially the same central wavelength.

3. Optical mapping apparatus according to claim 2, wherein the coherence length of at least one of said optical sources is electrically adjustable to provide either a continuous range for the compound source from less than a few micrometers or a few tens of micrometers, to more than a few hundreds of micrometers, or to provide adjustability on some subintervals, by applying a combination of currents thereto.

4. Optical mapping apparatus according to claim 2, wherein said optical source comprises an electronic unit, for changing the ratio of the powers of said two radiation sources;

wherein, when changing the ratio of the powers of said two superposed radiation sources, said electronic unit ensures that the overall intensity is kept constant, or that the bias intensity in the final image is kept constant.

5. Optical mapping apparatus according to claim 2, wherein the optical source comprises an electro-optic element for balancing the contribution of the two component sources in the final output beam.

6. Optical mapping apparatus according to claim 5, wherein said electro-optic element is an electrically controllable directional coupler.

7. Optical mapping apparatus according to claim 2, wherein said optical source comprises two first fibers, each said first fiber being arranged for transmitting light from a respective optical source, and a second fiber for collecting light from said source fibers, said second fiber being translatable between said first fibers.

8. Optical mapping apparatus according to claim 2, wherein said optical source comprises two first fibers, each first fiber being arranged for transmitting light from a respective one of said sources, and a collecting mirror for collecting light from said first fibers.

9. Optical mapping apparatus according to claim 3, wherein the output beams of said two superposed radiation sources are orientated and focused to ensure an intersection of areas of their spatial distribution power.

10. Optical mapping apparatus according to claim 2, comprising a translatable collecting fiber for collecting light from said optical sources.

11. Optical mapping apparatus according to claim 2, wherein said optical source with adjustable coherence length is a subnanosecond tunable optical source which is adapted to be tuned under subnanosecond electrical pulse control in a bandwidth for which the associated correlation profile width secures a predetermined depth resolution.

12. Optical mapping apparatus according to claim 2, wherein said first optical source of largest bandwidth is modulated in intensity at a first frequency, and the second source of narrowest bandwidth is modulated in intensity at a second frequency, said first and second frequencies being different, and their ratio being an irrational numeral, and wherein said photodetected signal is sent to a first receiver tuned on said first frequency and to a second receiver tuned on a second frequency, so as to select the corresponding images, where the first corresponding image has a very narrow sectioning interval given by said first receiver tuned on said the first frequency, and where the second corresponding image has a wider sectioning interval given by said second receiver tuned on said second frequency; and wherein said first and second corresponding images are displayed simultaneously by way of a two input display device.

13. Optical mapping apparatus according to claim 12, wherein the depth resolution in the final image or in the two or three images produced by the apparatus is adjustable by choosing a step chosen from the group of steps consisting of:
(i) adjusting the depth sectioning interval of a confocal optical receiver image;
(ii) varying the sectioning interval of one of the interferometer images by changing the coherence length of the source or of one of the sources; and
(iii) weighting the contributions of the interferometer and confocal optical receiver in a compound image, so as to provide an adjustable resolution depth from a minimum given by the minimum coherence length of the said first source to a maximum given by either the confocal optical receiver or the maximum coherence length of the said second source.

14. Optical mapping apparatus according to claim 1, wherein said optical source with adjustable coherence length is a multi-electrode laser diode.

15. Optical mapping apparatus according to claim 1, wherein there is a reference beam for said interferometer, and wherein said apparatus is further provided with a blocking means to block said reference beam, and wherein, when said blocking means is activated, it synchronously switches the input of the displaying device to the output of a high gain amplifier for the photodetected signal.

16. Optical mapping apparatus according to claim 15, where said interferometer uses balance detection, and wherein said amplifier provides the addition of the photodetected signals, the result of which is then sent to a displaying device.

17. Optical mapping apparatus according to claim 15, wherein, when said photodetectors are avalanche, their gain is switched automatically by a reference power via the voltage drop on series resistors connected therewith, said optical mapping apparatus is switched between a confocal regime of operation and an OCT regime of operation.

18. Optical mapping apparatus according to claim 15, wherein, when said interferometer is a bulk interferometer, the depth resolution of the image obtained with the reference arm blocked can be adjusted by varying the numerical aperture of optics preceding a photodetector, when the photodetector is used, or by simultaneously varying the numerical apertures of optics preceding two photodetectors when balance detection is employed, said numerical apertures being varied by adjusting either the focal length of the lenses or by adjusting the diameter of the pinhole in the optics preceding the photodetector, or photodetectors when balance detection is used.

19. Optical mapping apparatus according to claim 1, comprising a feedback loop under synchronous control of said raster scanning means for providing a curvature-corrected transversal image.

20. Optical mapping apparatus according to claim 1, wherein the means to alter the length of the reference beam comprises at least one galvanometer-mirror.

21. Optical mapping apparatus according to claim 20, wherein said means to alter the length of a reference beam for said interferometer comprises a galvanometer-mirror placed at a distance f+δ from a convergent lens, and a mirror at a distance f from said convergent lens, where f is the focal length of the convergent lens and where the incidence beam on the galvanometer-mirror is δ away from the galvanometer-mirror axis.

22. Optical mapping apparatus according to claim 20, wherein the means to alter the length of a reference beam for said interferometer comprises a galvanometer-mirror, a convergent lens, and a first mirror at a distance f away from the lens, and a second mirror to implement a double pass on the galvanometer-mirror and so as to increase the path variation;
wherein the point of incidence of a beam on the galvanometer-mirror is on its axis and in the focal plane of the lens; and
wherein the lens is laterally shifted in the plane of the scanned rays to ensure that, at the maximum angle of deviation, light reflected by said first mirror and refracted by the lens falls on said galvanometer-mirror.

23. Optical mapping apparatus according to claim 20, comprising a display scanning device in which a vertical display thereof performs in alternate directions which are changed at each change of a voltage ramp slope of a voltage applied to said galvanometer.

24. Optical mapping apparatus according to claim 23, where the galvanometer scanner giving the line in the raster can be used only to create the phase modulation to carry parts of the OCT image signal.

25. Optical mapping apparatus according to claim 24, where a combination of the modulation due to the galvanometer scanner giving the line in the raster, and of the modulation due to an extra phase modulator, is employed to carry all of the OCT image signal.

26. Optical mapping apparatus according to claim 24, where an electronic filter in a receiver may discard parts of the low frequency spectrum, and pass frequencies up to the maximum phase modulation frequencies resulting by the pass modulation introduced by transversal scanning the object.

27. Optical mapping apparatus according to claim 24, where the frequency of the carrier created by the said galvanometer scanner can be increased by shifting the incident optical beam away from the centre of the galvanometer mirror.

28. Optical mapping apparatus according to claim 20, wherein said means to alter the length of a reference beam for said interferometer comprises a first galvonmeter-mirror, a first convergent lens, a second galvonmeter-mirror, and a second convergent lens, where each respective lens is placed at a distance f+s from the respective galvonmeter-mirror, wherein f is the focal length of each respective convergent lens;
wherein the incidence beam on the first galvonmeter-mirror is redirected to said second galvonmeter-mirror and thence to a second optical output path.

29. Optical mapping apparatus according to claim 1, wherein said apparatus includes software which can generate a transversal image $O_s$ with different equivalent depth resolutions, by combining transversal OCT images collected at different depths, wherein said software generated image has a depth resolution between the minimum ensured by the coherence length of the optical source up to a maximum determined by the range of transversal images which have been collected; and wherein each image contribution to the final image is weighted according to a predetermined profile.

30. Optical mapping apparatus according to claim 1, where a processor can be introduced in each input of a display device to provide either a linear, logarithmic, or squared version of an input signal thereto.

31. Optical mapping apparatus with adjustable depth resolution, comprising:

an interferometer chosen from the group consisting of fiberized interferometers and bulk interferometers, wherein said interferometer is excited by an optical radiation source or a source with adjustable coherence length, said interferometer comprising a first optical path and a second optical path leading to an object location and to a reference reflector, respectively;

a confocal optical receiver with adjustable focal depth;

an optical splitter for internally directing light returned from an object situated at said object location to said optical confocal receiver;

raster scanning means for raster scanning an optical output from the interferometer over a line, or over a predetermined area;

interface optics for transferring an optical beam from said raster scanning means to the object and for transferring an optical output beam reflected and scattered from the object back to said optical splitter through said raster scanning means, and from said optical splitter to both of said interferometer and said optical confocal receiver, in a ratio determined by said optical splitter;

means to alter at least one of the first optical path and the second optical path, to introduce intensity modulation, or phase modulation, or intensity modulation and phase modulation;

analyzing means, coupled to said raster scanning means, for demodulating the photodetected signal;

means for longitudinal scanning, to alter the length of the first optical path or the second optical path over a predetermined amount, for at least one point in the raster, in steps or continuously, at a pace synchronised with transversal scanning means;

means for processing an image created by said interferometer and an image created by said confocal receiver; and means for the simultaneous display of the said respective images created by said interferometer and by said confocal receiver.

32. Optical mapping apparatus according to claim 31, wherein said optical source comprises two superposed radiation sources, one first said source having a very short coherence length, and the other second said source having a coherence length greater than that of the first said first source;

wherein both sources have substantially the same central wavelength.

33. Optical mapping apparatus according to claim 32, wherein the coherence length of at least one of said optical sources is electrically adjustable to provide either a continuous range for the compound source from less than a few micrometers or a few tens of micrometers, to more than a few hundreds of micrometers, or to provide adjustability on some subintervals, by applying a combination of currents thereto.

34. Optical mapping apparatus according to claim 32, wherein said optical source comprises an electronic unit, for changing the ratio of the powers of said two radiation sources;

wherein, when changing the ratio of the powers of said two superposed radiation sources, said electronic unit ensures that the overall intensity is kept constant, or that the bias intensity in the final image is kept constant.

35. Optical mapping apparatus according to claim 32, wherein the optical source comprises an electro-optic element for balancing the contribution of the two component sources in the final output beam.

36. Optical mapping apparatus according to claim 32, wherein said electro-optic element is an electrically controllable directional coupler.

37. Optical mapping apparatus according to claim 32, wherein said optical source comprises two first fibers, each said first fiber being arranged for transmitting light from a respective optical source, and a second fiber for collecting light from said source fibers, said second fiber being translatable between said first fibers.

38. Optical mapping apparatus according to claim 32, wherein said optical source comprises two first fibers, each first fiber being arranged for transmitting light from a respective one of said sources, and a collecting mirror for collecting light from said first fibers.

39. Optical mapping apparatus according to claim 32, wherein the output beams of said two superposed radiation sources are orientated and focused to ensure an intersection of areas of their spatial distribution power.

40. Optical mapping apparatus according to claim 32, comprising a translatable collecting fiber for collecting light from said optical sources.

41. Optical mapping apparatus according to claim 32, wherein said optical source with adjustable coherence length is a subnanosecond tunable optical source which is adapted to be tuned under subnanosecond electrical pulse control in a bandwidth for which the associated correlation profile width secures a predetermined depth resolution.

42. Optical mapping apparatus according to claim 32, wherein said first optical source of largest bandwidth is modulated in intensity at a first frequency, and the second source of narrowest bandwidth is modulated in intensity at a second frequency, said first and second frequencies being different, and their ratio being an irrational numeral, and wherein said photodetected signal is sent to a first receiver tuned on said first frequency and to a second receiver tuned on a second frequency, so as to select the corresponding images, where the first corresponding image has a very narrow sectioning interval given by said first receiver tuned on said the first frequency, and where the second corresponding image has a wider sectioning interval given by said second receiver tuned on said second frequency; and wherein said first and second corresponding images are displayed simultaneously by way of a three input display device.

43. Optical mapping apparatus according to claim 31, wherein said optical source with adjustable coherence length is a multi-electrode laser diode.

44. Optical mapping apparatus according to claim 31, wherein said optical source is broadband.

45. Optical mapping apparatus according to claim 31, wherein said optical splitter is a bulk beamsplitter.

46. Optical mapping apparatus according to claim 45, wherein said confocal receiver comprises an adjustable pinhole behind a lens or between lenses and a photodetector, and the focal depth interval is adjustable independently of the said interferometer.

47. Optical mapping apparatus according to claim 46, wherein said optical source is broadband, and wherein the depth resolution in a final image produced by said optical mapping apparatus is adjustable by choosing a step chosen from the group of steps consisting of:

(i) adjusting the depth sectioning interval of the image produced by the confocal optical receiver; and (ii) balancing the amplitudes of an interferometer image signal and of an optical confocal receiver signal sent to display means, so as to provide an adjustable resolution depth from a minimum given by the coherence length of the broadband source to a maximum given by the confocal optical receiver.

48. Optical mapping apparatus according to claim 46, wherein the depth resolution in a final image produced by the apparatus choosing a step chosen from the group of steps consisting of:

(i) adjusting the depth sectioning interval of a confocal optical receiver image;

(ii) varying the sectioning interval of an interferometer image by changing the coherence length of the source; and (iii) weighting the contributions of the interferometer and confocal optical receiver to a compound image, so as to provide an adjustable resolution depth from a minimum given by the minimum coherence length of said first source to a maximum given by either the confocal optical receiver or the maximum coherence length of said second source.

49. Optical mapping apparatus according to claim 45, wherein said confocal receiver comprises a fiber pigtail terminated on a photodetector.

50. Optical mapping apparatus according to claim 49, wherein said optical source is broadband;

wherein the depth resolution in a final image produced by said optical mapping apparatus is adjustable by balancing the amplitudes of an interferometer image signal and of an optical confocal receiver signal sent to a display means, so as to provide an adjustable resolution depth from a minimum given by the coherence length of the broadband source to a maximum given by the confocal optical receiver.

51. Optical mapping apparatus according to claim 31, wherein said optical splitter is a fiberized directional coupler terminated on a pigtailed photodetector provided on said optical confocal receiver, and wherein the fiber input of the directional coupler acts as the aperture of said confocal optical receiver, and said optical splitter is part of said first optical path of said interferometer.

52. Optical mapping apparatus according to claim 51, wherein said optical source is broadband;

wherein the depth resolution in a final image produced by said optical mapping apparatus is adjustable by balancing the amplitudes of an interferometer image signal and of an optical confocal receiver signal sent to a display means, so as to provide an adjustable resolution depth from a minimum given by the coherence length of the broadband source to a maximum given by the confocal optical receiver.

53. Optical mapping apparatus according to claim 51, wherein the depth resolution in a final image produced by the apparatus is adjustable by choosing a step from the group of steps consisting of:

(i) varying the sectioning interval of an image produced by the interferometer by changing the coherence length of the source; and (ii) weighting the contributions of the interferometer and confocal optical receiver, so as to provide an adjustable resolution depth from a minimum given by the minimum coherence length of the source to a maximum given by the confocal optical receiver.

54. Optical mapping apparatus according to claim 31, wherein the image given by said confocal optical receiver is used in the storage process of the image given by an OCT channel, to compensate during its acquisition, for the transversal object movement.

55. Optical mapping apparatus according to claim 54, wherein the means for processing images can perform mathematical operations in a pixel-by-pixel format using the image obtained by said image storage process.

56. Optical mapping apparatus according to claim 31, wherein the means for processing an image can perform mathematical operations in a pixel-by-pixel format using the interferometer image and the confocal optical receiver image.

57. Optical mapping apparatus according to claim 31, wherein there is a reference beam for said interferometer, and wherein said apparatus is further provided with a blocking means to block said reference beam, and wherein, when said blocking means is activated, it synchronously switches the input of the displaying device to the output of a high gain amplifier for the photodetected signal.

58. Optical mapping apparatus according to claim 57, wherein, when said interferometer is a bulk interferometer, the depth resolution of the image obtained with the reference arm blocked can be adjusted by varying the numerical aperture of optics preceding a photodetector, when the photodetector is used, or by simultaneously varying the numerical apertures of optics preceding two photodetectors when balance detection is employed, said numerical apertures being varied by adjusting either the focal length of the lenses or by adjusting the diameter of the pinhole in the optics preceding the photodetector, or photodetectors when balance detection is used.

59. Optical mapping apparatus according to claim 31, wherein said optical splitter has an optimized splitting ratio, so as to ensure optimal signal-to-noise ratios in images generated by both the interferometer and the optical confocal receiver.

60. Optical mapping apparatus according to claim 31, comprising a feedback loop under synchronous control of said raster scanning means for providing a curvature-corrected transversal image.

61. Optical mapping apparatus according to claim 31, wherein the means to alter the length of the reference beam comprises at least one galvanometer-mirror.

62. Optical mapping apparatus according to claim 61, wherein said means to alter the length of a reference beam for said interferometer comprises a galvanometer-mirror placed at a distance $f+\delta$ from a convergent lens, and a mirror at a distance f from said convergent lens, where f is the focal length of the convergent lens and where the incidence beam on the galvanometer-mirror is $\delta$ away from the galvanometer-mirror axis.

63. Optical mapping apparatus according to claim 61, wherein the means to alter the length of a reference beam for said interferometer comprises a galvanometer-mirror, a convergent lens, and a first mirror at a distance f away from the lens, and a second mirror to implement a double pass on the galvanometer-mirror and so as to increase the path variation;

wherein the point of incidence of a beam on the galvanometer-mirror is on its axis and in the focal plane of the lens; and wherein the lens is laterally shifted in the plane of the scanned rays to ensure that, at the maximum angle of deviation, light reflected by said first mirror and refracted by the lens falls on said galvanometer-mirror.

64. Optical mapping apparatus according to claim 61, comprising a display scanning device in which a vertical display thereof performs in alternate directions which are changed at each change of a voltage ramp slope of a voltage applied to said galvanometer.

65. Optical mapping apparatus according to claim 64, where the galvanometer scanner giving the line in the raster can be used only to create the phase modulation to carry parts of the OCT image signal.

66. Optical mapping apparatus according to claim 65, where a combination of the modulation due to the galvanometer scanner giving the line in the raster, and of the modulation due to an extra phase modulator, is employed to carry all of the OCT image signal.

67. Optical mapping apparatus according to claim 65, where an electronic filter in a receiver may discard parts of the low frequency spectrum, and pass frequencies up to the maximum phase modulation frequencies resulting by the pass modulation introduced by transversal scanning the object.

68. Optical mapping apparatus according to claim 65, where the frequency of the carrier created by the said galvanometer scanner can be increased by shifting the incident optical beam away from the centre of the galvanometer mirror.

69. Optical mapping apparatus according to claim 61, wherein said means to alter the length of a reference beam for said interferometer comprises a first galvonmeter-mirror, a first convergent lens, a second galvonmeter-mirror, and a second convergent lens, where each respective lens is placed at a distance f+s from the respective galvonmeter-mirror, wherein f is the focal length of each respective convergent lens;

wherein the incidence beam on the first galvonmeter-mirror is redirected to said second galvonmeter-mirror and thence to a second optical output path.

70. Optical mapping apparatus according to claim 31, wherein said apparatus includes software which can generate a transversal image $O_s$ with different equivalent depth resolutions, by combining transversal OCT images collected at different depths, wherein said software generated image has a depth resolution between the minimum ensured by the coherence length of the optical source up to a maximum determined by the range of transversal images which have been collected; and wherein each image contribution to the final image is weighted according to a predetermined profile.

71. Optical mapping apparatus according to claim 31, where a processor can be introduced in each input of a display device to provide either a linear, logarithmic, or squared version of an input signal thereto.

72. Optical mapping apparatus with adjustable depth resolution, comprising:

an interferometer chosen from the group consisting of fiberized interferometers and bulk interferometers, wherein said interferometer is excited by an optical source chosen from the group consisting of broadband optical sources and sources having adjustable coherence length;

wherein said interferometer comprises a first optical path and a second optical path leading to an object location, and to a reference reflector, respectively;

an optical element for producing an enlargement of the correlation function of the optical source when placed in either of said first path or said second path;

raster scanning means for transversally scanning an optical output from said interferometer over a predetermined area;

interface optics, for transferring an optical beam from said raster scanning means to an object situated at said object location, and for transferring an optical output beam reflected and scattered from said object back to said interferometer, along said first optical path;

means to alter at least one of said first optical path and said second optical path, to introduce intensity modulation, or phase modulation, or intensity modulation and phase modulation;

analyzing means, coupled to said raster scanning means, for demodulating the photodetected signal;

means for longitudinal scanning, to alter the length of the first optical path or the second optical path over a predetermined amount, for at least one point in the raster, in steps or continuously, at a pace synchronised with transversal scanning means; and means for displaying or storing an image of at least part of said object.

73. Optical mapping apparatus according to claim 72, wherein said optical element for enlarging the correlation profile of the optical source is a dispersive element which causes an increase in the associated coherence length.

74. Optical mapping apparatus according to claim 73, wherein said dispersive element can be gradually introduced into the first or second path for a continuous adjustment of the coherence length and consequently of the depth resolution in an image generated by said optical mapping apparatus.

75. Optical mapping apparatus according to claim 72, wherein said optical element for enlarging the correlation profile of the optical source is a multi-step echelon.

76. Optical mapping apparatus according to claim 72, comprising a feedback loop under synchronous control of said raster scanning means for providing a curvature-corrected transversal image.

77. Optical mapping apparatus according to claim 72, wherein the means to alter the length of the reference beam comprises at least one galvanometer-mirror.

78. Optical mapping apparatus according to claim 77, wherein said means to alter the length of a reference beam for said interferometer comprises a galvanometer-mirror placed at a distance f+δ from a convergent lens, and a mirror at a distance f from said convergent lens, where f is the focal length of the convergent lens and where the incidence beam on the galvanometer-mirror is δ away from the galvanometer-mirror axis.

79. Optical mapping apparatus according to claim 77, wherein the means to alter the length of a reference beam for said interferometer comprises a galvanometer-mirror, a convergent lens, and a first mirror at a distance f away from the lens, and a second mirror to implement a double pass on the galvanometer-mirror and so as to increase the path variation;

wherein the point of incidence of a beam on the galvanometer-mirror is of its axis and in the focal plane of the lens; and wherein the lens is laterally shifted in the plane of the scanned rays to ensure that, at the maximum angle of deviation, light reflected by said first mirror and refracted by the lens falls on said galvanometer-mirror.

80. Optical mapping apparatus according to claim 68, comprising a display scanning device in which a vertical display thereof performs in alternate directions which are changed at each change of a voltage ramp slope of a voltage applied to said galvanometer.

81. Optical mapping apparatus according to claim 80, where the galvanometer scanner giving the line in the raster can be used only to create the phase modulation to carry parts of the OCT image signal.

82. Optical mapping apparatus according to claim 81, where a combination of the modulation due to the galvanometer scanner giving the line in the raster, and of the modulation due to an extra phase modulator, is employed to carry all of the OCT image signal.

83. Optical mapping apparatus according to claim 81, where an electronic filter in a receiver may discard parts of the low frequency spectrum, and pass frequencies up to the maximum phase modulation frequencies resulting by the pass modulation introduced by transversal scanning the object.

84. Optical mapping apparatus according to claim 81, where the frequency of the carrier created by the said galvanometer scanner can be increased by shifting the incident optical beam away from the centre of the galvanometer mirror.

85. Optical mapping apparatus according to claim 77, wherein said means to alter the length of a reference beam for said interferometer comprises a first galvonmeter-mirror, a first convergent lens, a second galvonmeter-mirror, and a second convergent lens, where each respective lens is placed at a distance f+s from the respective galvonmeter-mirror, wherein f is the focal length of each respective convergent lens;
    wherein the incidence beam on the first galvonmeter-mirror is redirected to said second galvonmeter-mirror and thence to a second optical output path.

86. Optical mapping apparatus according to claim 72, wherein said apparatus includes software which can generate a transversal image $O_s$ with different equivalent depth resolutions, by combining transversal OCT images collected at different depths, wherein said software generated image has a depth resolution between the minimum depth resolution in a single OCT image up to a maximum determined by the range of depth wherefrom transversal images have been collected; and
    wherein each image contribution to the final image is weighted according to a predetermined profile.

87. Optical mapping apparatus according to claim 72, where a processor can be introduced in each input of a display device to provide either a linear, logarithmic, or squared version of an input signal thereto.

88. Optical mapping apparatus with adjustable depth resolution, comprising:
    at least two interferometers excited by an optical source consisting of broadband optical sources and sources having adjustable coherence length;
    wherein each of said interferometers comprises an at least partly common first optical path leading to an object location, and a respective second optical path for each interferometer, wherein each of said second optical paths leads to a respective reference reflector;
    at least one device for producing an enlargement of the correlation function of the source when placed in at least one of said optical second paths;
    adjustable raster scanning means for transversally scanning an optical output from said interferometers over a predetermined area;
    interface optics for transferring an optical beam from said raster scanning means to an object situated at the object location, and for transferring an optical output beam reflected and scattered from the object back to said interferometers, along said first optical path;
    means to alter said first optical path, or one of said second optical paths, to introduce intensity modulation, phase modulation, or intensity modulation and phase modulation;
    analyzing means, coupled to said raster scanning means, for demodulating the photodetected signal;
    longitudinal scanning means to alter the length of said first optical path or said second optical path in each interferometer simultaneously over a predetermined amount, for at least one point in the raster, in steps or continuously, at a pace synchronised with transversal scanning means; and
    means for displaying or storing two images of at least part of said object.

89. Optical mapping apparatus according to claim 88, wherein said first optical path is completely shared by said interferometers, and wherein said analyzing means uses a single photo receiver for all of said interferometers, and for each said second optical path;
    wherein said optical mapping apparatus comprises a phase modulator in each interferometer, where each respective phase modulation is driven at a different frequency sufficiently distant apart from the other respective phase modulation frequencies for said analyzing means to be able to separate the respective signals in said interferometers, by means of subsequent frequency band pass filtering.

90. Optical mapping apparatus according to claim 89, further comprising means for processing signals in said interferometers using mathematical operations in a pixel-by-pixel format in a controllable ratio using respective images created by each said interferometer.

91. Optical mapping apparatus according to claim 89, wherein said optical element for enlarging the correlation profile of said optical source can be gradually introduced into the second path of one of the interferometers, for continuous adjustment of the depth resolution of an image provided by that interferometer.

92. Optical mapping apparatus according to claim 89, wherein said optical element for enlarging the correlation profile of the optical source is a dispersive element which causes an increase in the associated coherence length.

93. Optical mapping apparatus according to claim 92, wherein an image in the one of the said interferometers which has the poorest depth resolution, obtained by using said optical element for enlarging the correlation profile, is used in a process for storing an image with the best depth resolution, obtained using another interferometer with no such optical element, in order to compensate for transversal object movement during image acquisition.

94. Optical mapping apparatus according to claim 89, wherein said optical element for enlarging the correlation profile of the optical source is a multi-step echelon.

95. Optical mapping apparatus according to claim 88, further comprising means for processing signals in said interferometers using mathematical operations in a pixel-by-pixel format in a controllable ratio using respective images created by each said interferometer.

96. Optical mapping apparatus according to claim 88, wherein said optical element for enlarging the correlation profile of said optical source can be gradually introduced into the second path of one of the interferometers, for continuous adjustment of the depth resolution of an image provided by that interferometer.

97. Optical mapping apparatus according to claim 88, wherein said optical element for enlarging the correlation profile of the optical source is a dispersive element which causes an increase in the associated coherence length.

98. Optical mapping apparatus according to claim 97, wherein an image in the one of the said interferometers which has the poorest depth resolution, obtained by using said optical element for enlarging the correlation profile, is used in a process for storing an image with the best depth resolution, obtained using another interferometer with no such optical element, in order to compensate for transversal object movement during image acquisition.

99. Optical mapping apparatus according to claim 88, wherein said optical element for enlarging the correlation profile of the optical source is a multi-step echelon.

100. Optical mapping apparatus according to claim 88, comprising a feedback loop under synchronous control of said raster scanning means for providing a curvature-corrected transversal image.

101. Optical mapping apparatus according to claim 88, wherein the means to alter the length of the reference beam comprises at least one galvanometer-mirror.

102. Optical mapping apparatus according to claim 101, wherein said means to alter the length of a reference beam for said interferometer comprises a galvanometer-mirror placed at a distance f+δ from a convergent lens, and a mirror at a distance f from said convergent lens, where f is the focal length of the convergent lens and where the incidence beam on the galvanometer-mirror is δ away from the galvanometer-mirror axis.

103. Optical mapping apparatus according to claim 101, wherein the means to alter the length of a reference beam for said interferometer comprises a galvanometer-mirror, a convergent lens, and a first mirror at a distance f away from the lens, and a second mirror to implement a double pass on the galvanometer-mirror and so as to increase the path variation;
  wherein the point of incidence of a beam on the galvanometer-mirror is on its axis and in the focal plane of the lens; and
  wherein the lens is laterally shifted in the plane of the scanned rays to ensure that, at the maximum angle of deviation, light reflected by said first mirror and refracted by the lens falls on said galvanometer-mirror.

104. Optical mapping apparatus according to claim 101, comprising a display scanning device in which a vertical display thereof performs in alternate directions which are changed at each change of a voltage ramp slope of a voltage applied to said galvanometer.

105. Optical mapping apparatus according to claim 104, where the galvanometer scanner giving the line in the raster can be used only to create the phase modulation to carry parts of the OCT image signal.

106. Optical mapping apparatus according to claim 105, where a combination of the modulation due to the galvanometer scanner giving the line in the raster, and of the modulation due to an extra phase modulator, is employed to carry all of the OCT image signal.

107. Optical mapping apparatus according to claim 105, where an electronic filter in a receiver may discard parts of the low frequency spectrum, and pass frequencies up to the maximum phase modulation frequencies resulting by the pass modulation introduced by transversal scanning the object.

108. Optical mapping apparatus according to claim 105, where the frequency of the carrier created by the said galvanometer scanner can be increased by shifting the incident optical beam away from the centre of the galvanometer mirror.

109. Optical mapping apparatus according to claim 101, wherein said means to alter the length of a reference beam for said interferometer comprises a first galvonmeter-mirror, a first convergent lens, a second galvonmeter-mirror, and a second convergent lens, where each respective lens is placed at a distance f+s from the respective galvonmeter-mirror, wherein f is the focal length of each respective convergent lens;
  wherein the incidence beam on the first galvonmeter-mirror is redirected to said second galvonmeter-mirror and thence to a second optical output path.

110. Optical mapping apparatus according to claim 88, where said optical mapping apparatus can be used to generate longitudinal images by using said transversal scanning means to generate a 1D sample over the object, and by replacing one of the transversal coordinates in the image with the longitudinal coordinate corresponding to the optical path difference introduced by said longitudinal scanning means.

111. Optical mapping apparatus according to claim 88, wherein said apparatus includes software which can generate a transversal image $O_s$ with different equivalent depth resolutions, by combining transversal OCT images collected at different depths, wherein said software generated image has a depth resolution between the minimum depth resolution in a single OCT image up to a maximum determined by the range of depth wherefrom transversal images have been collected; and
  wherein each image contribution to the final image is weighted according to a predetermined profile.

112. Optical mapping apparatus according to claim 88, where a processor can be introduced in each input of a display device to provide either a linear, logarithmic, or squared version of an input signal thereto.

\* \* \* \* \*